(12) United States Patent
Gronvald et al.

(10) Patent No.: US 6,645,953 B2
(45) Date of Patent: *Nov. 11, 2003

(54) MEIOSIS REGULATING COMPOUNDS

(75) Inventors: Frederik Christian Gronvald, Vedbaek (DK); Peter Faarup, Vaerlose (DK); Erling Guddal, Brondby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/878,884

(22) Filed: Jun. 11, 2001

(65) Prior Publication Data

US 2002/0013302 A1 Jan. 31, 2002

Related U.S. Application Data

(63) Continuation-in-part of application No. 09/436,810, filed on Nov. 9, 1999, now abandoned, which is a continuation-in-part of application No. 08/973,661, filed as application No. PCT/DK96/00273 on Jun. 21, 1996, now abandoned.

(30) Foreign Application Priority Data

| Jun. 23, 1995 | (DK) | ............................................. 0728/95 |
| Jun. 23, 1995 | (DK) | ............................................. 0730/95 |
| Dec. 22, 1995 | (DK) | ............................................. 1461/95 |

(51) Int. Cl.[7] ............................................. A61K 31/56
(52) U.S. Cl. ...................... 514/169; 514/177; 514/178; 514/179; 514/182; 514/841; 514/842; 514/843
(58) Field of Search ................................ 514/169, 177, 514/178, 179, 182, 841, 842, 843

(56) References Cited

U.S. PATENT DOCUMENTS

| 5,364,847 A | | 11/1994 | Labrie et al. |
| 5,716,777 A | * | 2/1998 | Byskov et al. ................. 435/2 |

FOREIGN PATENT DOCUMENTS

| HU | 200 203 | 6/1986 |
| HU | 214 873 | 1/1991 |
| WO | WO 96/00235 | 1/1996 |

OTHER PUBLICATIONS

Parish, et al., STERIODS, vol. 48, pp. 407–418 (1986).
Anastasia, et al., J. Chem. Soc., vol. 1, pp. 587–590, (1983).
Parish, et al., STEROIDS, pp. 579–596, (1989).
Patterson, et al., J. Org. Chem., vol. 44, No. 11, pp. 1866–1871 (1979).
Frelek et al., Tetrahed, vol. 2, No. 5, pp. 381–387 (1991).
Bird et al., J. Chem. Soc., pp. 4728–4755 (1979).
Kim et al., Bioorg. Med. Chem., vol., 3 No. 4, pp. 367–374 (1995).
Dolle et al., J. Chem. Soc. Chem. Comm., vol. 19, pp. 133–135 (1988).
Byskov et al., The Physiology of Reproduction, vol. 2nd Ed., Ch. 9, pp. 487–540 (1994).
Grant et al., Aust. J. Chem., vol. 38, pp. 1505–1519 (1985).
Boar et al., J. Chem. Soc., vol. 1, pp. 1237–1241 (1975).
Barton et al., J. Chem. Soc., vol. 1, pp. 251–259 (1987).
Arunachalam et al., The Journal of Org. Chem., vol. 46, pp. 2966–2968 (Feb. 20, 1981).
Dolle et al., The Journal of Organic Chem., vol. 51, pp. 4047–4053 (1986).
Fieser et al., J. AM. Chem. Soc., vol. 75, pp. 4719–4722 (1953).
Fieser, J. AM. Chem Soc., vol. 75, pp. 4395–4423 (1953).
Byskov et al., Nature, vol. 374, pp. 559–562 (Apr. 6, 1995).
Byskov et al., Dev. Biol., vol. 52, pp. 193–200 (1976).
Downs, Mol. Reprod. Dev., vol. 35, pp. 82–94 (1993).
Eppig et al., Dev. Biol., vol. 119, pp. 313–321 (1987).
Downs, Dev. Biol., vol. 82, pp. 454–458 (Jan. 1985).
Christian Grøndahl et al., Human Reproduction, "Human Oocyte Maturation in vitro is stimulated by meiosis–activating sterol"., vol. 15, Part 5, pp. 3–10 (2000).
Christa Hegele–Hartung et al., Biology of Reproduction, "Activation of Meiotic Maturation in Rat Oocytes After Treatment with Follicular Fluid Meiosis–Activating Sterol in Vitro and Ex Vitro", vol. 64, pp. 418–424 (2001).
Christa Hegele–Hartung et al., Biology of Reproduction, "Nuclear and Cytoplasmic Maturation of Mouse Oocytes After Treatment with Synthetic Meiosis–Activating Sterol In Vitro[1]", vol. 64, pp. 1362–1372 (1999).
Grøndahl et al., Biology of Reproduction, Meiosis–activating sterol Promotes resumption of meiosis in mouse oocytes cultured in vitro in Contrast to related oxysterols (In Process Citation) vol. 58(5) pp. 1297–1302 (1998).

* cited by examiner

*Primary Examiner*—Barbara P. Badio
(74) *Attorney, Agent, or Firm*—Reza Green, Esq.; Richard W. Book, Esq.; Marc A. Began, Esq.

(57) ABSTRACT

Sterol derivative compounds, structurally related to natural compounds which can be extracted from bull testes and from human follicular fluid, useful for regulating meiosis in oocytes and in male germ cells. Some of these compounds are useful in the treatment of infertility, whereas other compounds are useful as contraceptives.

12 Claims, No Drawings

MEIOSIS REGULATING COMPOUNDS

CROSS-REFERENCE TO RELATED APPLICATIONS

This is a continuation-in-part application of U.S. application Ser. No. 09/436,810 filed Nov. 9, 1999, now abandoned, which is a continuation-in-part of Ser. No. 08/973,661 filed Dec. 19, 1997, now abandoned, which is a 35 U.S.C. 371 national application of PCT/DK96/00273 filed Jun. 21, 1996, and claims priority under 35 U.S.C. 119 of Danish applications 0728/95 filed Jun. 23, 1995, 0730/95 filed Jun. 23, 1995 and 1461/95 filed Dec. 22, 1995, the contents of which are fully incorporated herein by reference.

FIELD OF THE INVENTION

The present invention relates to pharmacologically active compounds and to their use as medicaments. More particularly it has been found that the sterol derivatives of the invention are useful for regulating meiosis.

BACKGROUND

Meiosis is the unique and ultimate event of germ cells on which sexual reproduction is based. Meiosis comprises two meiotic divisions. During the first division, exchange between maternal and paternal genes take place before the pairs of chromosomes are separated into the two daughter cells. These contain only half the number (1n) of chromosomes and 2c DNA. The second meiotic division proceeds without a DNA synthesis. This division therefore results in the formation of the haploid germ cells with only 1c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted. Meiosis in females is not completed until after fertilization, and results in only one ovum and two abortive polar bodies per germ cell. In contrast, only some of the male germ cells enter meiosis from puberty and leave a stem population of germ cells throughout life. Once initiated, meiosis in the male cell proceeds without significant delay and produces four spermatozoa.

Only little is known about the mechanisms which control the initiation of meiosis in the male and in the female. In the oocyte, new studies indicate that follicular purines, hypoxanthine or adenosine, could be responsible for meiotic arrest (Downs, S M et al. *Dev Biol* 82 (1985) 454–458; Eppig, J J et al. *Dev Biol* 119 (1986) 313–321; and Downs, S M *Mol Reprod Dev* 35(1993) 82–94).

SUMMARY OF THE INVENTION

The instant invention provides compounds and methods useful for relieving infertility in females and males, particularly in mammals, more particularly in humans. These compounds and methods are useful as contraceptives in females and males, particularly in mammals, more particularly in humans. Further, methods are described for using the instant compounds for regulating meiosis in oocytes and in male germ cells.

In its broadest aspect, the present invention relates to compounds of formula (I)

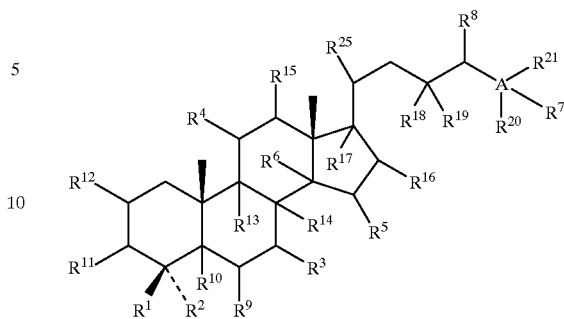

(I)

wherein $R^1$ and $R^2$, independently, are selected from the group consisting of hydrogen and branched or unbranched $C_1$–$C_6$ alkyl which may be substituted by halogen, hydroxy or cyano, or wherein $R^1$ and $R^2$ together designate methylene or, together with the carbon atom to which they are bound, form a cyclopropane ring, a cyclopentane ring, or a cyclohexane ring; $R^3$ is selected from the group consisting of hydrogen, methylene, hydroxy, methoxy, acetoxy, oxo, =NOR$^{26}$ wherein $R^{26}$ is hydrogen or $C_1$–$C_3$ alkyl, halogen, and hydroxy and $C_1$–$C_4$ alkyl bound to the same carbon atom of the sterol skeleton, or designates, together with $R^9$ or $R^{14}$, an additional bond between the carbon atoms to which $R^3$ and $R^9$ or $R^{14}$ are bound; $R^4$ is selected from the group consisting of hydrogen, methylene, hydroxy, methoxy, acetoxy, oxo, =NOR$^{27}$ wherein $R^{27}$ is hydrogen or $C_1$–$C_3$ alkyl, halogen, and hydroxy and $C_1$–$C_4$ alkyl bound to the same carbon atom of the sterol skeleton, or $R^4$ designates, together with $R^{13}$ or $R^{15}$, an additional bond between the carbon atoms to which $R^4$ and $R^{13}$ or $R^{15}$ are bound; $R^5$ is selected from the group consisting of hydrogen, $C_1$–$C_4$ alkyl, methylene, hydroxy, methoxy, oxo, and =NOR$^{22}$ wherein $R^{22}$ is hydrogen or $C_1$–$C_3$ alkyl, or $R^5$ designates, together with $R^6$, an additional bond between the carbon atoms to which $R^5$ and $R^6$ are bound; $R^6$ is hydrogen or $R^6$ designates, together with $R^5$, an additional bond between the carbon atoms to which $R^5$ and $R^6$ are bound; $R^9$ is hydrogen or $R^9$ designates, together with $R^3$ or $R^{10}$, an additional bond between the carbon atoms to which $R^9$ and $R^3$ or $R^{10}$ are bound; $R^{10}$ is hydrogen or $R^{10}$ designates, together with $R^9$, an additional bond between the carbon atoms to which $R^{10}$ and $R^9$ are bound; $R^{11}$ is selected from the group consisting of hydroxy, alkoxy, substituted alkoxy, acyloxy, sulphonyloxy, phosphonyloxy, oxo, =NOR$^{28}$ wherein $R^{28}$ is hydrogen or $C_1$–$C_3$ alkyl, halogen and hydroxy and $C_1$–$C_4$ alkyl bound to the same carbon atom of the sterol skeleton, or $R^{11}$ designates, together with $R^{12}$, an additional bond between the carbon atoms to which $R^{11}$ and $R^{12}$ are bound; $R^{12}$ is selected from the group consisting of hydrogen, $C_1$–$C_3$ alkyl, vinyl, $C_1$–$C_3$ alkoxy and halogen, or $R^{12}$ designates, together with $R^{11}$, an additional bond between the carbon atoms to which $R^{12}$ and $R^{11}$ are bound; $R^{13}$ is hydrogen or $R^{13}$ designates, together with $R^4$ or $R^{14}$, an additional bond between the carbon atoms to which $R^{13}$ and $R^4$ or $R^{14}$ are bound; $R^{14}$ is hydrogen or $R^{14}$ designates, together with $R^3$, $R^6$ or $R^{13}$, an additional bond between the carbon atoms to which $R^{14}$ and $R^3$ or $R^6$ or $R^{13}$ are bound; $R^{15}$ is selected from the group consisting of hydrogen, $C_1$–$C_4$ alkyl, methylene, hydroxy, methoxy, acetoxy, oxo, and =NOR$^{23}$ wherein $R^{23}$ is hydrogen or $C_1$–$C_3$ alkyl, or $R^{15}$ designates, together with $R^4$, an additional bond between the carbon atoms to which $R^{15}$ and $R^4$ are bound; $R^{16}$ is selected from the group consisting of hydrogen, $C_1$–$C_3$ alkyl, methylene, hydroxy, methoxy, oxo and =NOR$^{24}$ wherein R$^{24}$ is hydrogen or $C_1$–$C_3$ alkyl, or R$^{16}$ designates, together with R$^{17}$, an additional bond between the carbon atoms to which R$^{16}$ and R$^{17}$ are bound; R$^{17}$ is hydrogen or R$^{17}$ designates, together with R$^{16}$, an additional bond between the carbon atoms to which R$^{17}$ and R$^{16}$ are bound; R$^{18}$ and R$^{19}$ are independently hydrogen or fluoro; R$^{25}$ is selected from the group consisting of $C_{1-4}$alkyl, methylene, hydroxy and oxo; A is a carbon atom or a nitrogen atom; when A is a carbon atom, R$^7$ is selected from the group consisting of hydrogen, hydroxy and fluoro, and R$^8$ is selected from the group consisting of hydrogen, $C_1$–$C_4$ alkyl, methylene and halogen, or R$^7$ designates, together with R$^8$, an additional bond between the carbon atoms to which R$^7$ and R$^8$ are bound; R$^{20}$ is selected from the group consisting of $C_1$–$C_4$ alkyl, trifluoromethyl and $C_3$–$C_6$ cycloalkyl and R$^{21}$ is selected from the group consisting of $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl, or R$^{20}$ and R$^{21}$, together with the carbon atom to which they are bound, form a $C_3$–$C_6$ cycloalkyl ring; and when A is a nitrogen atom, R$^7$ designates a lone pair of electrons and R$^8$ is selected from the group consisting of hydrogen, $C_1$–$C_4$ alkyl and oxo; R$^{20}$ and R$^{21}$ are, independently, $C_1$–$C_4$ alkyl or $C_3$–$C_6$ cycloalkyl; provided that the compound of formula (I) does not have any cumulated double bonds and further provided that the compound is not one of the following compounds:

Cholest-7-ene-3β-ol;
4-Methylcholest-7-ene-3β-ol;
4-Ethylcholest-7-ene-3β-ol;
4,4-Dimethylcholest-7-ene-3β-ol;
4α-Methyl-4β-ethylcholest-7-ene-3β-ol;
4α-Ethyl-4β-methylcholest-7-ene-3β-ol;
4,4-Diethylcholest-7-ene-3β-ol;
4-Propylcholest-7-ene-3β-ol;
4-Butylcholest-7-ene-3β-ol;
4-Isobutylcholest-7-ene-3β-ol;
4,4-Tetramethylenecholest-7-ene-3β-ol;
4,4-Pentamethylenecholest-7-ene-3β-ol;
Cholest-8-ene-3β-ol;
4-Methylcholest-8-ene-3β-ol;
4-Ethylcholest-8-ene-3β-ol;
4,4-Dimethylcholest-8-ene-3β-ol;
4α-Methyl-4β-ethylcholest-8-ene-3β-ol;
4α-Ethyl-4β-methylcholest-8-ene-3β-ol;
4,4-Diethylcholest-8-ene-3β-ol;
4-Propylcholest-8-ene-3β-ol;
4-Butylcholest-8-ene-3β-ol;
4-Isobutylcholest-8-ene-3β-ol;
4,4-Tetramethylenecholest-8-ene-3β-ol;
4,4-Pentamethylenecholest-8-ene-3β-ol;
Cholest-8(14)-ene-3β-ol;
4-Methylcholest-8(14)-ene-3β-ol;
4-Ethylcholest-8(14)-ene-3β-ol;
4,4-Dimethylcholest-8(14)-ene-3β-ol;
4α-Methyl-4β-ethylcholest-8(14)-ene-3β-ol;
4α-Ethyl-4β-methylcholest-8(14)-ene-3β-ol;
4,4-Diethylcholest-8(14)-ene-3β-ol;
4-Propylcholest-8(14)-ene-3β-ol;
4-Butylcholest-8(14)-ene-3β-ol;
4-Isobutylcholest-8(14)-ene-3β-ol;
4,4-Tetramethylenecholest-8(14)-ene-3β-ol;
4,4-Pentamethylenecholest-8(14)-ene-3β-ol;
Cholesta-8,14-diene-3β-ol;
4-Methylcholesta-8,14-diene-3β-ol;
4-Ethylcholesta-8,14-diene-3β-ol;
4,4-Dimethylcholesta-8,14-diene-3β-ol;
4α-Methyl-4β-ethylchlolesta-8,14-diene-3β-ol;
4α-Ethyl-4β-methylcholesta-8,14-diene-3β-ol;
4,4-Diethylcholesta-8,14-diene-3β-ol;
4-Propylcholesta-8,14-diene-3β-ol;
4-Butylcholesta-8,14-diene-3β-ol;
4-Isobutylcholesta-8,14-diene-3β-ol;
4,4-Tetramethylenecholesta-8,14-diene-3β-ol;
4,4-Pentamethylenecholesta-8,14-diene-3β-ol;
Cholesta-8,24-diene-3β-ol;
4-Methylcholesta-8,24-diene-3β-ol;
4-Ethylcholesta-8,24-diene-3β-ol;
4,4-Dimethylcholesta-8,24-diene-3β-ol;
4α-Methyl-4β-ethylcholesta-8,24-diene-3β-ol;
4α-Ethyl-4β-methylcholesta-8,24-diene-3β-ol;
4,4-Diethylcholesta-8,24-diene-3β-ol;
4-Propylcholesta-8,24-diene-3β-ol;
4-Butylcholesta-8,24-diene-3β-ol;
4-Isobutylcholesta-8,24-diene-3β-ol;
4,4-Tetramethylenecholesta-8,24-diene-3β-ol;
4,4-Pentamethylenecholesta-8,24-diene-3β-ol;
Cholesta-8,14,24-triene-3β-ol;
4-Methylcholesta-8,14,24-triene-3β-ol;
4-Ethylcholesta-8,14,24-triene-3β-ol;
4,4-Dimethylcholesta-8,14,24-triene-3β-ol;
4α-Methyl-4βethylcholesta-8,14,24-triene-3β-ol;
4α-Ethyl-4βmethylcholesta-8,14,24-triene-3β-ol;
4,4-Diethylcholesta-8,14,24-triene-3β-ol;
4-Propylcholesta-8,14,24-triene-3β-ol
4-Butylcholesta-8,14,24-triene-3β-ol;
4-Isobutylcholesta-8,14,24-triene-3β-ol;
4,4-Tetramethylenecholesta-8,14,24-triene-3β-ol; and
4,4-Pentamethylenecholesta-8,14,24-triene-3β-ol;

and esters and ethers thereof, and further provided that the compound of formula (I) is not a compound of formula (II)

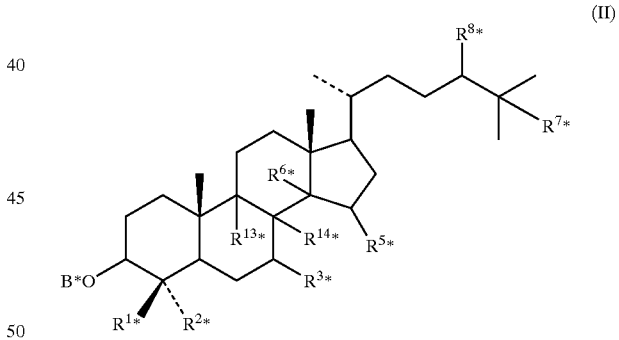

wherein R$^{1*}$ and R$^{2*}$, independently, are selected from the group consisting of hydrogen, branched or unbranched $C_1$–$C_6$ alkyl which may be substituted by halogen or hydroxy or wherein R$^{1*}$ and R$^{2*}$, together with the carbon atom to which they are bound, form a cyclopentane ring or a cyclohexane ring; R$^{13*}$ and R$^{14*}$ together designate an additional bond between the carbon atoms to which they are bound in which case R$^{3*}$ is hydrogen and R$^{6*}$ and R$^{5*}$ are either hydrogen or together they designate an additional bond between the carbon atoms to which they are bound; or R$^{3*}$ and R$^{14*}$ together designate an additional are either hydrogen or together they designate an additional bond between the carbon atoms to which they are bound; or R$^{6*}$ and R$^{14*}$ together designate an additional bond between the carbon atoms to which they are bound in which case R$^{13*}$, R$^{3*}$ and R$^{5*}$ are all hydrogen; R$^{8*}$ and R$^{7*}$ are hydrogen or together they designate an additional bond between the carbon atoms to which they are bound; and B* is either hydrogen or an acyl group, including a sulphonyl group or a phosphonyl group, or a group which together with the remaining part of the molecule forms an ether.

In seperate and more specific embodiments, the compound of formula (I) above is a compound wherein: $R^1$ and $R^2$ are both hydrogen; one of $R^1$ and $R^2$ is hydrogen while the other is methyl; wherein $R^1$ and $R^2$ are both methyl; $R^1$ is branched or unbranched $C_1$-$C_6$ alkyl, optionally substituted by halogen, hydroxy or cyano; $R^2$ is branched or unbranched $C_1$-$C_6$ alkyl, optionally substituted by halogen, hydroxy or cyano; $R^1$ and $R^2$ together designate methylene wherein $R^1$ and $R^2$, together with the carbon atom to which they are bound, form a cyclopropane ring; $R^1$ and $R^2$, together with the carbon atom to which they are bound, form a cyclopentane ring; $R^1$ and $R^2$, together with the carbon atom to which they are bound, form a cyclohexane ring.

In further specific embodiments, the compound of formula (I) above is a compound wherein $R^3$ is hydrogen; methylene; hydroxy; methoxy or acetoxy; halogen; oxo; or =NOH. In one embodiment, $R^3$ is =NOR$^{26}$ wherein $R^{26}$ is $C_1$-$C_3$ alkyl. In further specific embodiments, $R^3$ is hydroxy and $C_1$-$C_4$ alkyl bound to the same carbon atom of the sterol skeleton; $R^3$, together with $R^9$, designates an additional bond between the carbon atoms to which $R^3$ and $R^9$ are bound; and $R^3$, together with $R^{14}$, designates an additional bond between the carbon atoms to which $R^3$ and $R^{14}$ are bound;.

In specific embodiments, the compound of formula (I) above is a compound wherein $R^4$ is one of hydrogen, methylene, hydroxy, methoxy, acetoxy, oxo, =NOH, =NOR$^{27}$, wherein $R^{27}$ is $C_1$-$C_3$ alkyl. In further embodiments, the compound of formula (I) above is a compound wherein $R^4$ is hydroxy and $C_1$-$C_4$ alkyl bound to the same carbon atom of the sterol skeleton; $R^4$, together with $R^{13}$, designates an additional bond between the carbon atoms to which $R^4$ and $R^{13}$ are bound; or $R^4$, together with $R^{15}$, designates an additional bond between the carbon atoms to which $R^4$ and $R^{15}$ are bound.

In specific embodiments, the compound of formula (I) above is a compound wherein $R^5$ is one of hydrogen, $C_1$-$C_4$ alkyl, methylene, hydroxy; methoxy; oxo; =NOH; or $R^5$ is =NOR$^{22}$, wherein $R^{22}$ is $C_1$-$C_3$ alkyl; or $R^5$, together with $R^6$, designates an additional bond between the carbon atoms to which $R^5$ and $R^6$ are bound.

In specific embodiments, the compound of formula (I) above is a compound wherein $R^6$ is hydrogen; or wherein $R^6$, together with $R^{14}$, designates an additional bond between the carbon atoms to which $R^6$ and $R^{14}$ are bound.

In specific embodiments, the compound of formula (I) above is a compound wherein $R^9$ is hydrogen, or wherein $R^9$, together with $R^{10}$, designates an additional bond between the carbon atoms to which $R^9$ and $R^{10}$ are bound.

In another specific embodiment, the compound of formula (1) above is a compound wherein $R^{10}$ is hydrogen.

In another specific embodiment, the compound of formula (I) above is a compound wherein $R^{11}$ is one of hydroxy; alkoxy, aralkyloxy, alkoxyalkoxy or alkanoyloxyalkyl, each group comprising a total of up to 10 carbon atoms, preferably up to 8 carbon atoms; $C_1$-$C_4$ alkoxy; methoxy; ethoxy; CH$_3$OCH$_2$O—; pivaloyloxymethoxy; an acyloxy group derived from an acid having from 1 to 20 carbon atoms; an acyloxy group selected from the group consisting of acetoxy, benzoyloxy, pivaloyloxy, butyryloxy, nicotinoyloxy, isonicotinoyloxy, hemi succinoyloxy, hemi glutaroyloxy, butylcarbamoyloxy, phenylcarbamoyloxy, butoxy carbonyloxy, tert-butoxycarbonyloxy and ethoxycarbonyloxy; sulphonyloxy; phosphonyloxy; oxo; or =NOH. In another related embodiment, the compound of formula (I) above is a compound wherein $R^{11}$ is =NOR$^{28}$, wherein $R^{28}$ is $C_1$-$C_3$ alkyl. In further embodiments, $R^{11}$ is halogen; or $R^{11}$ is hydroxy and $C_1$-$C_4$ alkyl bound to the same carbon atom of the sterol skeleton; or $R^{11}$, together with $R^{12}$, designates an additional bond between the carbon atoms to which $R^{11}$ and $R^{12}$ are bound.

In further embodiments, $R^{12}$ is one of hydrogen.; $C_1$-$C_3$ alkyl; $C_1$-$C_3$ alkoxy; or halogen.

In another embodiments, the compound of formula (I) above is a compound wherein $R^{13}$ is hydrogen; or wherein $R^{13}$, together with $R^{14}$, designates an additional bond between the carbon atoms to which $R^{13}$ and $R^{14}$ are bound.

In further embodiments, the compound of formula (I) above is a compound wherein $R^{14}$ is hydrogen.

In another embodiment, the compound of formula (I) above is a compound wherein $R^{15}$ is one of hydrogen; $C_1$-$C_4$ alkyl; methylene; hydroxy; $R^{15}$ is methoxy or acetoxy; oxo; =NOH; or $R^{15}$ is =NOR$^{23}$, wherein $R^{23}$ is $C_1$-$C_3$ alkyl.

In further embodiments, the compound of formula (I) above is a compound wherein $R^{16}$ is one of hydrogen; $C_1$-$C_3$ alkyl; methylene; hydroxy; methoxy; oxo; or =NOH; or a compound wherein $R^{16}$ is =NOR$^{24}$, wherein $R^{24}$ is $C_1$-$C_3$ alkyl; or wherein $R^{16}$, together with $R^{17}$, designates an additional bond between the carbon atoms to which $R^{16}$ and $R^{17}$ are bound.

In another embodiment, the compound of formula (I) above is a compound wherein $R^{17}$ is hydrogen or hydroxy.

In another embodiment, the compound of formula (I) above is a compound wherein $R^{18}$ and $R^{19}$ are both hydrogen; or wherein $R^{18}$ and $R^{19}$ are both fluoro; or one of $R^{18}$ and $R^{19}$ is fluoro and the other is hydrogen.

In another embodiment, the compound of formula (I) above is a compound wherein $R^{25}$ is one of hydrogen; $C_1$-$C_4$ alkyl; methylene; hydroxy; or oxo.

In further related embodiments, the compound of formula (I) above is a compound wherein A is a carbon atom; A is a carbon atom and $R^7$ is hydrogen; A is a carbon atom $R^7$ is hydroxy; A is a carbon atom $R^7$ is fluoro; A is a carbon atom $R^7$, together with $R^8$, designates an additional bond between the carbon atoms to which $R^7$ and $R^8$ are bound; A is a carbon atom $R^8$ is hydrogen; A is a carbon atom $R^8$ is $C_1$-$C_4$ alkyl; A is a carbon atom $R^8$ is methylene; A is a carbon atom $R^8$ is halogen; A is a carbon atom $R^{20}$ is $C_1$-$C_4$ alkyl; A is a carbon atom $R^{20}$ is trifluoromethyl; A is a carbon atom $R^{20}$ is $C_3$-$C_6$ cycloalkyl; A is a carbon atom $R^{21}$ is $C_1$-$C_4$ alkyl; A is a carbon atom $R^{21}$ is $C_1$-$C_4$ hydroxyalkyl; A is a carbon atom $R^{21}$ is $C_1$-$C_4$ haloalkyl containing up to three halogen atoms; A is a carbon atom $R^{21}$ is acetoxymethyl; A is a carbon atom $R^{21}$ is methoxymethyl; A is a carbon atom and $R^{21}$ is $C_3$-$C_6$ cycloalkyl; A is a carbon atom and $R^{20}$ and $R^{21}$, together with the carbon atom to which they are bound, form a $C_3$-$C_6$ cycloalkyl ring, preferably a cyclopropyl ring, a cyclopentyl ring or a cyclohexyl ring; A is a nitrogen and $R^7$ designates a lone pair of electrons.

In another more specific embodiment, the compound of formula (I) above is a compound wherein A is a nitrogen atom, $R^7$ designates a lone pair of electrons and $R^8$ is hydrogen; A is a nitrogen atom, $R^7$ designates a lone pair of electrons and $R^8$ is $C_1$-$C_4$ alkyl; A is a nitrogen atom, $R^7$ designates a lone pair of electrons and $R^8$ is oxo; or A is a nitrogen atom, $R^7$ designates a lone pair of electrons and $R^{20}$ and $R^{21}$, independently, are selected from the group consisting of $C_1$-$C_4$ alkyl, cyclopropyl, cyclopentyl and cyclohexyl.

In a further aspect, the present invention relates to the use of a compound of formula (I) above as a medicament, in particular as a medicament for use in the regulation of meiosis. The compound may be used neat or in the form of a liquid or solid composition containing auxiliary ingredients conventionally used in the art.

DETAILED DESCRIPTION

The presence of a diffusible meiosis regulating substance was first described by Byskov et al. in a culture system of fetal mouse gonads (Byskov, A G et al. *Dev Biol* 52 (1976) 193–200). A meiosis activating substance (MAS) was secreted by the fetal mouse ovary in which meiosis was ongoing, and a meiosis preventing substance (MPS) was released from the morphologically differentiated testis with resting, non-meiotic germ cells. It was suggested that the relative concentrations of MAS and MPS regulated the beginning, arrest and resumption of meiosis in the male and in the female germ cells (Byskov, A G et al. in *The Physiology of Reproduction* (eds. Knobil, E and Neill, J D, Raven Press, New York (1994)). A recent article (Byskov, A G et al. *Nature* 374 (1995) 559–562) describes the isolation from bull testes and from human follicular fluid of certain sterols that activate oocyte meiosis. Unfortunately, these sterols are rather labile and utilization of the interesting finding would thus be greatly facilitated if more stable meiosis activating compounds were available.

In the present context, the expression "regulating the meiosis" is used to indicate that compounds of the invention can be used for stimulating the meiosis, including in vitro, in vivo, or ex vivo use. Thus, the compounds which agonists of a naturally occurring meiosis activating substance, can be used in the treatment of infertility which is due to insufficient stimulation of meiosis in females and in males. Other compounds of the invention, which are antagonists of a naturally occurring meiosis activating substance, can be used for regulating meiosis, preferably in vivo, such that they are suitable as contraceptives. In this case the "regulation" means partial or total inhibition.

In one aspect of the invention, compounds of formula (I) above are useful in a method for regulation of the meiosis of an oocyte, in particular a mammalian oocyte, more particularly a human oocyte.

In one embodiment, a compound of formula (J) above is useful in methods for stimulating the meiosis of an oocyte, in particular a mammalian oocyte, more particularly a human oocyte. In another embodiment, a compound of formula (I) above is useful in methods for inhibiting the meiosis of an oocyte, in particular a mammalian oocyte, more particularly a human oocyte.

In a related aspect, the present invention relates to the use of a compound of formula (I) above in the regulation of the meiosis of a male germ cell, in particular a mammalian male germ cell, more particularly a human male germ cell. In one embodiment, a compound of formula (I) above is useful in methods for stimulating of the meiosis of a male germ cell, in particular a mammalian male germ cell, more particularly a human male germ cell. In another embodiment, a compound of formula (I) above is useful in a method for inhibiting the meiosis of a male germ cell, in particular a mammalian male germ cell, more particularly a human male germ cell.

In one aspect, the present invention encompasses methods of regulating meiosis in a mammalian germ cell, comprising administering an effective amount of a compound of formula (I) above to a germ cell in need of such a treatment. In one aspect, the compound is administered to the germ cell by administering the compound to a mammal hosting said cell. In specific embodiments, the germ cell is an oocyte or a male germ cell. In more specific embodiments, the compound is administered to the oocyte ex vivo. In another specific embodiment, the compound is administered to immature male germ cells in vitro to produce mature male germ cells. In a further specific embodiment, the immature male germ cells are contained in testicular tissue.

Methods of Controlling Meiosis

Controlling of meiosis is achieved as described in Examples 41–46 (below) using the compounds described herein that stimulate or induce meiosis (agonists of the naturally occurring meiosis activating sterols), or the compounds described herein that counteract or inhibits meiosis (antagonist of the naturally occurring meiosis activating sterols).

The timing and the compound's effect is pivotal for obtaining the desired objective whether this is to treat or relieve infertility or whether this is to obtain a safe and efficacious novel contraceptive method.

Definitions

As used in the present description and claims, the expression $C_1$–$C_3$ alkyl designates an alkyl group having from one to three carbon atoms; preferred examples are methyl, ethyl and propyl, more preferred methyl and ethyl. Similarly, the expression $C_1$–$C_4$ alkyl designates an alkyl group having from one to four carbon atoms; preferred examples are methyl, ethyl, propyl, isopropyl and butyl, more preferred methyl and ethyl. The expression $C_1$–$C_6$ alkyl designates an alkyl group having from one to six carbon atoms; preferred examples are methyl, ethyl, propyl, isopropyl, butyl, tert-butyl, pentyl and hexyl, more preferred methyl, ethyl, propyl, isopropyl, butyl and tert-butyl, still more preferred methyl and ethyl.

As used in the present description and claims, the expression $C_1$–$C_3$ alkoxy designates an alkoxy group having from one to three carbon atoms; preferred examples are methoxy, ethoxy and propoxy, more preferred methoxy and ethoxy.

As used in the present description and claims, the expression halogen preferably designates fluoro and chloro, more preferred fluoro.

The compounds of the invention have a number of chiral centers in the molecule and thus exist in several isomeric forms. All these isomeric forms and mixtures thereof are within the scope of the invention.

The compounds of the present invention will influence the meiosis in oocytes as well as in male germ cells.

General

The existence of a meiosis inducing substance in nature has been known for some time. However, until recently the identity of the meiosis inducing substance or substances was unknown. The possibility of being able to influence the meiosis are several. According to a preferred embodiment of the present invention, the instant compounds are used to stimulate the meiosis. According to another preferred embodiment of the present invention, the instant compounds are used to stimulate the meiosis in humans. Thus, these compounds are promising as new fertility regulating agents without the usual side effect on the somatic cells which are known from the hitherto used hormonal contraceptives which are based on estrogens and/or gestagens.

For use as a contraceptive agent in females, a meiosis inducing substance can be administered so as to prematurely induce resumption of meiosis in oocytes while they are still in the growing follicle, before the ovulatory peak of gonadotropins occurs. In women, the resumption of the meiosis can, for example, be induced a week after the preceding menstruation has ceased. When ovulated, the resulting overmature oocytes are then most likely not to be fertilized. The normal menstrual cycle is not likely to be affected. In this connection it is important to notice, that the biosynthesis of progesterone in cultured human granulosa cells (somatic cells of the follicle) is not affected by the presence of a meiosis inducing substance whereas the estrogens and gestagens used in the hitherto used hormonal contraceptives do have an adverse effect on the biosynthesis of progesterone.

According to another aspect of this invention, a meiosis inducing substance of the instant invention can be used in the treatment of certain cases of infertility in females, including women, by administration thereof to females who, due to an insufficient own production of meiosis activating substance, are unable to produce mature oocytes. Also, when in vitro fertilization is performed, better results are achieved, when a compound of claim 1 is added to the medium in which the oocytes are kept.

When infertility in males, including men, is caused by an insufficient own production of the meiosis activating substance and thus a lack of mature sperm cells, administration of a compound of the invention may relieve the problem.

As an alternative to the method described above, contraception in females can also be achieved by administration of the instant compound which inhibits meiosis, so that no mature oocytes are produced. Similarly, contraception in males can be achieved by administration of a compound of the instant invention which inhibits the meiosis, so that no mature sperm cells are produced.

The route of administration of compositions containing a compound of the instant invention may be any route which effectively transports the active compound to its site of action. Thus, when the compounds of this invention are to be administered to a mammal, they are conveniently provided in the form of a pharmaceutical composition which comprises at least one compound of the instant invention in connection with a pharmaceutically acceptable carrier. For oral use, such compositions are preferably in the form of capsules or tablets.

From the above it will be understood that the administrative regimen called for will depend on the condition to be treated. Thus, when used in the treatment of infertility the administration may have to take place once only, or for a limited period, e.g. until pregnancy is achieved. When used as a contraceptive, the compounds will either have to be administered continuously or cyclically. When used as a contraceptive by females and not taken continuously, the timing of the administration relative to the ovulation will be important.

Pharmaceutical compositions comprising a compound of the instant invention may further comprise carriers, diluents, absorption enhancers, preservatives, buffers, agents for adjusting the osmotic pressure, tablet disintegrating agents and other ingredients which are conventionally used in the art. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions. Such liquid compositions may be suitable for injection or for use in connection with ex vivo and in vitro fertilization. The liquid compositions may contain other ingredients which are conventionally used in the art, some of which are mentioned in the list above.

Further, a composition for transdermal administration of a compound of this invention may be provided in the form of a patch and a composition for nasal administration may be provided in the form of a nasal spray in liquid or powder form.

The dose of a compound of the invention to be used will be determined by a physician and will depend, inter alia, on the particular compound employed, on the route of administration and on the purpose of the use.

The instant compounds may be synthesized by methods known per se.

The present invention is further illustrated by the following examples which, however, are not to be construed as limiting the scope of protection. The features disclosed in the foregoing description and in the following examples may, in any combination thereof, be material for realizing the invention in diverse forms thereof.

EXAMPLES

Example 1

Preparation of 7-oxo-5α-cholest-8-ene-3β-ol.

0.50 g of 3β-acetoxy-7-oxo-5α-cholest-8-ene (Fieser, L F *J Am Chem Soc* (1953) 4395) was refluxed in a mixture of 30 ml of ethanol and 20 ml of 1 M aqueous sodium hydroxide for 1 hour. After cooling to room temperature, 23 ml of 1M hydrochloric acid and 100 ml of water were added. After cooling on an ice bath, the precipitate was filtered off, washed with water and dried to give 0.435 g of the crude compound which was purified by chromatography on silica gel (methylene chloride/methanol, 40:1 (w/w)) and crystallized from methanol/water to give 0.198 g of the title compound. Melting point: 115–117° C. The $^1$H-NMR spectrum (CDCl$_3$,d) showed characteristic signals at: 0.59 (s,3H); 1.18 (s,3H); 3.64 (m,$^1$H). The $^{13}$C-NMR spectrum (CDCl$_3$, 100.6 MHz) showed characteristic signals at: 69.5; 132.8; 164.8; 198.6.

Example 2

Preparation of 7-oxo-5α-cholesta-8,14-diene-3β-ol.

The compound was prepared as described by Fieser, L F et al. *J Am Chem Soc* (1953) 4719) and showed the following characteristic physical constants: Melting point: 140–142° C. $^1$H-NMR spectrum (CDCl$_3$,d): 0.79 (s,3H), 1.14 (s,3H), 3.66 (m,1H), 6.45 (s,1H). $^3$C-NMR spectrum (CDCl$_3$, 100.6 MHz): 69.4; 126.1; 126.6; 140.8; 164.9; 197.2.

Example 3

Preparation of 7α-methyl-5a-cholest-8-ene-3b,7b-diol.

0.50 g of 3b-acetoxy-7-oxo-5α-cholest-8-ene (Fieser, L F *J Am Chem Soc* (1953) 4395) was dissolved in 10 ml of tetrahydrofuran and 3 ml of 3M methylmagnesium chloride in tetrahydrofuran was added dropwise at 0° C. over 15 minutes. The mixture was stirred at room temperature for 1 hour, cooled to 0° C., and 50 ml of a 1M solution of ammonium chloride was added dropwise over 5 minutes. The mixture was extracted twice with 50 ml of ethylacetate. The combined organic phases were washed with water and brine and evaporated to yield 474 mg of the crude product which was crystallized from ethylacetate/heptane to yield 168 mg of the title compound. From the mother liquor another crop (107 mg) of the title compound was isolated. Melting point: 92–94° C. The $^1$H-NMR spectrum (CDCl$_3$,d) showed characteristic signals at: 0.69 (s,3H), 1.03 (s,3H), 1.37 (s,3H), 3.62 (m,1H). The $^{13}$C-NMR spectrum (CDCl$_3$, 50.3 MHz) showed characteristic signals at: 70.7; 73.8; 132.9; 139.2.

Example 4

Preparation of 11-oxo-5α-cholest-8-ene-3-ol.

This compound was prepared as described by Parish, E S et al. *Steroids* 48 (1986) 407) and showed physical constants as described in the literature.

Example 5

Preparation of 3β-Hydroxy-5α-cholest-8-ene-7-oxime.

0.25 g of 7-oxo-5α-cholest-8-ene-3β-ol (cf. Example 1) was dissolved in 10 ml of dry pyridine. 0.43 g of hydroxylamine hydrochloride was added, and the mixture was stirred at 70° C. for 3 hours. After evaporation to dryness, the residue was triturated with water to give 238 mg of the crude product. Recrystallization from methanol yielded 164 mg of the title compound. Melting point: 218–223° C. The $^1$H-NMR spectrum (CDCl$_3$,d) showed characteristic signals at: 0.62 (s,3H), 1.03 (s,3H), 3.0 (dd, 1H), 3.62 (m, 1H), 7.52 (broad s, 1H).

The $^{13}$C-NMR spectrum (CDCl$_3$, 100.6 MHz) showed characteristic signals at: 69.9, 126.7, 149.8, 157.7.

Example 6

Preparation of 3β-acetoxy-7-oxo-5α-cholest-8-ene.

This compound was prepared as described by Fieser, L F *J Am Chem Soc* (1953) 4395 and showed physical constants as described in the literature.

Example 7
Preparation of 3β-acetoxy-7-oxo-5α-cholesta-8,14-diene.

This compound was prepared as described by Fieser, L F et al. *J Am Chem Soc* (1953)4719 and showed physical constants as described in the literature.

Example 8
Preparation of 7-oxo-5α-cholest-8-ene-3β-yl benzoate.

This compound was prepared as described by Parish E J et al. *Steroids* 48 (1986) 407 and showed physical constants as described in the literature.

Example 9
Preparation of 7-methylene-5α-cholest-9-ene-3β-ol.

0.54 g of sodium hydride (60%) was dissolved in 10 ml of dimethyl sulfoxide at 70° C. After 15 minutes a solution of 5.24 g of methyltriphenylphosphonium bromide in 33 ml of dimethyl sulfoxide and then a solution of 3β-acetoxy-7-oxo-5α-cholest-8-ene (cf. Example 6) in 28 ml benzene was added. The mixture was stirred at 60° C. for 22 hours, cooled to room temperature, poured on 1M hydrochloride acid/ice, and extracted several times with benzene. The combined organic phases were evaporated to dryness and the residue was dissolved in a mixture of methanol/water/cyclohexane, 13:7:20 (w/w). The methanol/water phase was extracted several times with cyclohexane and the combined cyclohexane phases were evaporated to dryness to give 1.32 g of an oil which was dissolved in 15 ml of heptane, filtered and evaporated to dryness. The residue (0.80 g) was chromatographed on 40 g silica gel (toluene/ethylacetate, 9:1 (w/w)) to give 247 mg of an almost pure product, which was crystallized from methanol to yield 110 mg of the title compound. Melting point: 44–50° C.

The $^1$H-NMR spectrum (CDCl$_3$,d) showed characteristic signals at: 0.65 (s,3H); 1.06 (s,3H); 2.62 (d,1H); 3.58 (m,1H); 4.68 (d,2H); 5.27 (d,1H). The $^{13}$C-NMR spectrum (CDCl$_3$, 100.6 MHz) showed characteristic signals at: 70.5; 105.2; 115.7; 146.1; 150.5.

Example 10
Preparation of 7-methyl-5α-cholesta-6,8-diene-3β-ol.

0.90 g of 7a-methyl-5α-cholest-8-ene-3β,7β-diol (cf. Example 3) was suspended in 55 ml of formic acid and stirred overnight at room temperature. The mixture was poured on ice water and the precipitated compound was filtered off, washed with water, and dried. The residue (0.84 g) was refluxed in a mixture of 50 ml ethanol and 25 ml 1 M aqueous sodium carbonate for 15 minutes. The solvent was evaporated and the residue was redissolved in methylene chloride and water. The organic phase was evaporated to dryness and crystallized from ethanol/water to yield 395 mg of the title compound. Melting point: 112–113° C. The $^1$H-NMR spectrum (CDCl$_3$,d) of the product showed characteristic signals at: 0.58 (s,3H), 0.88 (s,3H), 1.83 (s,3H), 3.58 (m,1H), 5.37 (d,1H). The $^{13}$C-NMR spectrum (CDCl$_3$, 100.6 MHz) showed characteristic signals at: 70.9, 116.6, 129.0, 129.6, 145.3.

Example 11
Preparation of 11-oxo-5α-cholest-8-ene-3β-yl benzoate.

This compound was prepared as described by Parish, E J et al. Steroids 48 (1986) 407) and showed physical constants as described in literature.

Example 12
Preparation of cholesta-8,14-diene-5α-H-3-one.

Cholesta-8,14-diene-5a-3-one was prepared according to Dolle *J Org Chem* 51 (1986) 4047–4053. The product showed the following physical characteristics: $^1$H-NMR: Hd: 5.78 (d 1H, C4H), 5.16 (1H, m, C7H). Elementary analysis: Cal: C: 84.7; H: 11.1; O: 4.18; Found: C: 84.7; H: 11.4.

Example 13
Preparation of 3α-flourocholesta-8,14-diene.

Cholesta-8,14-diene-3β-ol (1.17 g, 3 mmol) was dissolved in 10 ml of methylenechloride and cooled to −78° C. Over 10 min a solution of diethylaminosulfur trifluoride (1.4 g, 8.7 mmol) in 10 ml of methylenechloride was added at −78° C. The mixture was stirred for 1½ hour at −78° C. and was then slowly heated to room temperature. To the reaction mixture was added 15 ml of water while stirring was continued. The organic phase was separated and washed with 30 ml of 5% NaHCO$_3$ and then with water. The organic phase was dried with MgSO$_4$ and evaporated to dryness. The residue was purified by column chromatography using heptane for a first fraction and heptane/acetone, 95:5 (w/w) for a second fraction containing 3α-fluorocholesta-8,14 diene, 0.14 g (12%). Melting point: 98.6° C. Elementary analysis: Cal C: 83.88; H: 11.21; F: 4.91. Found C: 83.92; H: 11.75. $^{19}$F-NMR: d 181.0 and 181.2 ($J_{HCF}$ 45.2 Hz, C$_3$-aF).

Example 14
Preparation of cholesta-2,8,14-triene.

The title compound was prepared by using a method analogous to a method described in *J Chemical Research* (miniprint) (1979) 4714–4755. Cholesta-8,14-diene-3β-ol (1.17 g, 3 mmol) was dissolved in 10 ml of methylenechloride and cooled to −78° C. Over 10 min a solution of diethylaminosulfur trifluoride (1.4 g, 8,7 mmol) in 10 ml of methylenechloride was added at −78° C. The mixture was stirred and was then slowly heated to the room temperature. The reaction mixture was added 15 ml water while stirring was continued. The organic phase was separated and washed with 30 ml of 5% NaHCO$_3$ and then with water. The organic phase was dried with MgSO$_4$ and evaporated to dryness. The residue was purified by column chromatography using heptane for a first fraction A giving cholesta-2,8,14-triene, 0.23 g. Melting point: 104.7° C. Elementary analysis: Cal C: 88.45; H: 11.55. Found C: 88.58; H: 11.89. NMR: Hd: 5.64 (m 2H; C$_2$—H; C$_3$—H)d 5.35 (s,1H C 15H). Cd: 125.95 (C$_3$), 125.67 (C$_2$).

Example 15
Preparation of cholesta-8,14-diene-5α(H)-3-(E),(Z)-oxime.

Cholesta-8,14-diene-3-one (1.0 g, 2.61 mmol) was dissolved in 15 ml of pyridine and hydroxylamine, HCl (0.29 g, 4.23 mmol) was added. The reaction mixture was heated at 70–72° C. for 1½ hour while stirred. The reaction mixture was cooled and evaporated to dryness. 30 ml of 50% acetic acid/water was added and the crystals formed were separated by filtration. The crystals were dissolved in heptane and washed with water. The organic phase was separated and evaporated to dryness. The crystals were recrystallized from ethanol to give 0.91 g of 5α-cholesta-8,14-diene-3-(E) and (Z)-oxime. Elementary analysis: Cal C: 81.55; H: 10.90; N: 3.52; 0: 4.02. Found: 81.65; H: 11.30; N: 3.43. $^{13}$C-NMR: d 159,66 and 159.51 (3-C).

Example 16
3β-Hydroxy-4,4-dimethyl-5α-chola-8,14-dien-24-oic acid-N,N-dimethyl amide.

3β-tert-butyldimethylsilyloxy-4,4-dimethyl-5α-chola-8,14-dien-24 oic acid (0.30 g) is dissolved in 10 ml of dry dichloromethane. After cooling to −15° C., 0.07 ml of N-methylmorpholine and 0.084 ml of isobutylchloroformate is added and the mixture is stirred at −15° C. for 20 minutes, whereupon 1.74 ml of a 2.0 M solution of N,N-dimethylamine in THF) is added. The mixture is stirred overnight and the temperature is slowly elevated to room temperature. After aqueous work-up and crystallization from methanol, 3β-tert-butyldimethylsilyloxy-4,4-dimethyl-5α-chola-8,14-dien-24 oic acid-N,N-dimethyl amide (0,231 g) is obtained. M.p. 143–145° C. $^1$H-NMR (CDCl$_3$, 400

MHz)): δ=5.35 (1H, s); 3.20 (1H, m); 3.03 (3H, s); 2.95 (3H, s); 0.90 (9H, s); 0.05 (6H, m).

3β-tert-butyldimethylsilyloxy-4,4-dimethyl-5α-chola-8,14-dien-24 oic acid-N,N-dimethyl amide (0.10 g) is dissolved in 5 ml of ethanol, 0.2 ml of 6N hydrogen chloride is added and the mixture is stirred at room temperature the weekend over. The product is precipitated with 10 ml of water, filtered and recrystallized from ethanol/heptan to give the title compound (59 mg). M.p. 192–195° C. $^1$H-NMR (CDCl$_3$, 400 MHz)): δ=5.36 (1H, s); 3.24 (1H, m); 3.02 (3H, s); 2.94 (3H, s). Molecular weight: Calculated: 427.7. Found (by mass spectroscopy): 427.4.

Example 17
4,4-Dimethyl-24-dimethylamino-5α-chola-8,14-dien-3β-ol.

The compound is synthesised by lithium aluminium hydride reduction in THF of 3β-hydroxy-4,4-dimethyl-5α-chola-8,14-dien-24-oic acid-N,N-dimethyl amide. $^1$H-NMR (CDCl$_3$, 400 MHz): δ=5.35 (1H, s); 3.23 (1H, m); 2.85 (2H, m); 2.72 (6H, s).

Example 18
Synthesis of 4,4-dimethyl-(25R)-26-hydroxycholest-5-en-3-one
Step 1.

A mixture of (25R)-Cholest-5-ene-3β,26-diol (6.24 g, 15.4 mmol), imidazole (4.21 g, 61 mmol) and tert-butyldimethylsilylchloride (2.34 g, 15.4 mmol) and dimethylformamide was heated to 60° C. for 1.5 hours, then poured into water (300 ml) and extracted with diethyl ether (5×100 ml). Flash chromatography afforded (25R)-26-(tert-butyldimethylsilyloxy)cholest-5-en-3β-ol (5.09 g). Melting point: 93.5° C. The $^1$H-NMR spectrum (CDCl$_3$, d) showed characteristic signals at: 0.01 (s, 6H), 0.63 (s, 3H), 0.90 (s, 9H), 3.4 (m, 3H, H-26 and H-3), 5.32 (d, 1H, H-6). The $^{13}$C-NMR spectrum (CDCl$_3$, d) showed characteristic signals at: 50.1 (C-9), 56.1 (C14), 56.7 (C-17), 68.5 (C-26), 71.7 (C-3), 121.6 (C-6), 140.7 (C-5). The mass spectrum showed characteristic peaks at: 516.5 (M$^+$).
Step 2.

A mixture of (25R)-26-(tert-butyldimethylsilyloxy)cholest-5-en-3β-ol (7.4g, 14.3mmol) and 1-methylpiperidone (55 mL) in toluene (550 mL) was heated to reflux temperature and 100ml toluene was distilled off. Aluminium triisopropyl oxide (15 g, 1377 mmol) was then added portionwise over 10 minutes and the whole heated at refux for 4 hours. After cooling, water (300 mL) was added and the aqueous layer separated and extracted with diethyl ether (5×100 mL). The combined organic layers were washed with water (2×60 mL), dried over magnesium sulphate and concentrated to give residue which was purified by flash chromatography to give 6.26 g (25R)-26-(tert-Butyldimethylsilyloxy)-cholest-4-en-3-one (6.26 g).
The $^1$H-NMR spectrum (CDCl$_3$, d) showed characteristic signals at: 0.01 (s, 6H), 0.66 (s, 3H), 0.89 (s, 9H), 3.35 (m, 2H, H-26), 5.67 (s, 1H, H4). The $^{13}$C-NMR spectrum (CDCl$_3$, d) showed characteristic signals at: 53.7 (C-9), 55.8 (C-14), 56.0 (C-17), 68.5 (C-26), 123.7 (C4), 171.6 (C-5), 199.8 (C-3). The mass spectrum showed characteristic peaks at: 515.4 (M$^+$).
Step 3.

To a stirred suspension of KOtBu (13.17 g, 117 mmol) in tBuOH (300 mL) at 45° C. was added (25R)-26-(tert-butyldimethylsilyloxy)cholest-4-en-3-one (12 g, 23.5 mmol) and the whole stirred for 10 minutes. Iodomethane (18 ml) was added and the reaction stirred a further 0.5 hour, concentrated to one third the original volume and poured into 500 mL ice water. Extraction with diethyl ether, drying over magnesium sulphate and concentration gave a residue which was purified by flash chromatography to give 4,4-dimethyl-(25R)-26-(tert-Butyldimethylsilyloxy)cholest-4-en-3-one (8.88 g).

The $^1$H-NMR spectrum (CDCl$_3$, d) showed characteristic signals at: 0.02 (s, 6H), 0.65 (s, 3H), 0.89 (s, 9H), 3.35 (m, 2H, H-26), 5.52 (m, 1H, H-6). The $^{13}$C-NMR spectrum (CDCl$_3$, d) showed characteristic signals at: 49.0 (C-9), 56.2 (C-14), 56.8 (C-17), 68.6 (C-26), 120.0 (C-6), 149.8 (C-5), 216.8 (C-3). The mass spectrum showed characteristic peaks at: 543.4 (M$^+$).
Step 4.

A solution of 4,4-dimethyl-(25R)-26-(tert-butyldimethylsilyloxy)cholest-4-en-3-one (86 mg, 0.17 mmol) and tetrabutyl ammonium fluoride (140 mg, 0.53 mmol) in THF (2mL) was stirred for 2 hours at room temperature. Removal of solvent under reduced pressure gave a residue which was purified by flash chromatography to give 4,4-dimethyl-(25R)-26-hydroxycholest-5-en-3-one (47 mg).

The $^1$H-NMR spectrum (CDCl$_3$, d) showed characteristic signals at: 0.65 (s, 3H), 0.72 (s, 3H), 0.88 (s, 3H), 0.91 (s, 3H), 2.50 (m, 2H, H-2), 3.42 (m, 2H, H-26), 5.52 (m, 1H, H-6).

The $^{13}$C-NMR spectrum (CDCl$_3$, d) showed characteristic signals at: 49.3 (C-9), 56.5 (C-14), 57.1 (C-17), 68.8 (C-26), 120.3 (C-6), 150.1 (C-5), 217.1 (C-3). The mass spectrum showed characteristic peaks at: 428.3 (M$^+$).

Example 19
4,4-Dimethyl-(25R)-cholest-5-ene-3β,26-diol
Step 1.

To a suspension of lithium aluminium hydride (0.76 g, 20 mmol) in THF (60 mL) at ice bath temperature was added 4,4-dimethyl-(25R)-26-(tert-butyldimethylsilyloxy)cholest-4-en-3-one (8.58 g, 15 mmol) in THF (50 mL). After 1.5 hours the reaction was quenched with water, and the whole filtered through a plug of Celite. Concentration under reduced pressure gave a residue which was dissolved in dichloromethane, dried over magnesium sulphate, and purified by flash chromatography to give 3β-hydroxy-4,4-dimethyl-(25R)-26-(tert-butyldimethylsilyloxy)cholest-5-ene (7.3 g).

Melting point 88.5° C. The $^1$H-NMR spectrum (CDCl$_3$, d) showed characteristic signals at: 0.02 (s, 6H), 0.63 (s, 3H), 0.90 (s, 9H), 3.3 (m, 3H, H-26 and H-3), 5.52 (m, 1H, H-6). The $^{13}$C-NMR spectrum (CDCl$_3$, d) showed characteristic signals at: 50.7 (C-9), 55.9 (C-14), 57.1 (C-17), 68.4 (C-26), 77.4 (C-3), 120.0(C-6), 149.6 (C-5). The mass spectrum showed characteristic peaks at: 544.4 (M$^+$).
Step 2.

Silyl deprotection of 3β-hydroxy-4,4-dimethyl-(25R)-26-(tert-butyldimethylsilyloxy)cholest-5-ene (60 mg, 0.11 mmol) with tetrabutyl ammonium fluoride and recrystallisation from methanol to give 4,4-dimethyl-(25R)-cholest-5-ene-3β,26-diol (30 mg).

Melting point: 174–175° C. The $^1$H-NMR spectrum (CDCl$_3$, d) showed characteristic signals at: 0.65 (s, 3H), 0.90 (s, 3H), 0.92 (s, 3H), 1.03 (s, 3H), 1.05 (s, 3H), 1.14 (s, 3H), 1.23 (s, 3H), 3.22 (1 H, s, H-3), 3.45 (m, 2H, H-26), 5.53 (m, 1H, H-6). The mass spectrum showed characteristic peaks at: 430.4 (M$^+$).

Example 20
4,4-Dimethyl-(25R)-cholest-5,7-diene-3β,26β-diol
Step 1.

A mixture of 3β-hydroxy-4,4-dimethyl-(25R)-26-(tert-butyldimethylsilyloxy)-cholest-5-ene (7.2 g, 13.2 mmol), tert-butyldimethylsilylchloride (3.99 g, 26mmol) and imidazole (4.49 g, 66 mmol) in THF (250 mL) were heated for 16 hours at 60° C., poured into water (300 mL) and extracted with diethyl ether. Concentration under reduced pressure and chromatography gave 3β-(25S)-26-bis(tert-butyldimethylsilyloxy)-4,4-dimethylcholest-5-ene (8.26 g).

Melting point: 97.0° C. The H-NMR spectrum (CDCl$_3$, d) showed characteristic signals at: 0.02 (s, 12H), 0.63 (s, 3H), 0.90 (s, 18H), 3.15 (m, 1H, H-3), 3.39 (m, 2H, H-26), 5.52 (m, 1H, H-6). The $^{13}$C-NMR spectrum (CDCl$_3$, d) showed characteristic signals at: 50.8 (C-9), 55.9 (C-14), 57.1 (C-17), 68.3 (C-26), 77.7 (C-3), 119.5 (C-6), 150.1 (C-5). The mass spectrum showed characteristic peaks at: 658.5 (M$^+$).

Step 2.

A mixture of 3β-(25S)-26-bis(tert-butyldimethylsilyloxy)-4,4-dimethylcholest-5-ene (4.2 g, 6.37 mmol) and 1,3-dibromo-5,5-dimethylhydantoin (1.63 g, 5.73 mmol) in benzene (150 mL) and hexane (60 mL) was heated at reflux temperature for 0.5 hour. After cooling, the solid material was removed by filtration and the organic phase concentrated under reduced pressure. Quinaldine (9 mL) and o-xylene (250 mL) was added and the whole heated at 140° C. for 0.5 hour. Concentration of the reaction mixture and chromatography gave 3β-(25S)-26-bis(tert-butyldimethylsilyloxy)-4,4-dimethylcholest-5,7-diene (4.4 g).

The $^1$H-NMR spectrum (CDCl$_3$, d) showed characteristic signals at: 0.02 (s, 12H), 0.63 (s, 3H), 0.90 (s, 18H), 3.35 (m, 3H, H-26 and H-3), 5.52 (m, 1H, H-6), 5.87 (d, 1H, H-7). The $^{13}$C-NMR spectrum (CDCl$_3$, d) showed characteristic signals at: 47.0 (C-9), 54.2 (C-14), 55.6 (C-17), 68.3 (C-26), 77.5 (C-3), 117.4 (C-7), 118.7 (C-7), 141.1 (C-8), 150.7 (C-5). The mass spectrum showed characteristic peaks at: 656.6 (M$^+$).

Step 3.

Hydrogen fluoride (4 mL of 40% w/w in water) and 3β-(25 S)-26-bis(tert-butyldimethylsilyloxy)-4,4-dimethylcholest-5,7-diene (30 mg, 0.05 mmol) in acetonitrile (3 mL) was stirred for 16 hours at room temperature. The reaction was quenched with saturated ammonium carbonate (50 mL) and the product extracted with dichloromethane, purified by flash chromatography and recrystallized from methanol to give 4,4-dimethyl-(25R)-cholest-5,7-diene-3β,26β-diol (17 mg).

Melting point: 168.5–169° C. The $^1$H-NMR spectrum (CDCl$_3$, d) showed characteristic signals at: 0.58 (s, 3H), 0.90 (s, 3H), 0.92 (s, 3H), 0.94 (s, 3H), 0.98 (s, 3H), 1.10 (s, 3H), 1.18 (s, 3H), 3.45 (m, 3H, H-26 and H-3), 5.53 (m, 1H, H-6), 5.90 (d, 1H, H-7). The mass spectrum showed characteristic peaks at: 428.3 (M$^+$).

Example 21

(25R)-4,4-Dimethyl-5α-cholesta-8,14-diene-3β,26-diol

A mixture of 3β-(25R)-26-bis(tert-butyldimethylsilyloxy) 4,4-dimethylcholest-5,7-diene (450 mg, 0.83 mmol), concentrated HCl (6 mL), benzene (6 mL) and ethanol (25 mL) were heated to reflux temperature for 5 hours. After cooling the reaction was concentrated to half volume, and water (35 mL) added. The crystalline precipitate thus formed was collected by filtration, dried under vacuum and recrystallized from ethyl acetate to give the title compound (150 mg).

Melting point: 180–181° C. The $^1$H-NMR spectrum (CDCl$_3$, d) showed characteristic signals at: 0.80 (s, 3H), 0.82 (s, 3H), 0.90 (s, 3H), 0.93 (s, 3H), 0.95 (s, 3H), 1.02 (s, 3H), 1.05 (s, 3H), 3.22 (dd, 1H, H-3), 3.43 (m, 2H, H-26), 5.33 (m, 1H, H-15). The $^{13}$C-NMR spectrum (CDCl$_3$, d) showed characteristic signals at: 68.4 (C-26), 78.7 (C-3), 117.4 (C-1S), 122.8 (C-14), 141.8 (C-9), 151.1 (C-8). The mass spectrum showed characteristic peaks at: 428.4 (M$^+$).

Example 22

(25R)-26-Chloro-4,4-dimethyl-5α-cholesta-8,14-dien-3β-ol

Step 1.

A solution of (25R)-3β-(tert-butyldimethylsilyloxy)-4,4-dimethylcholest-5,7-dien-26-ol (0.5 g, 0.92 mmol) and p-toluene sulphonylchloride (0.55 g, 2.8 mmol) in pyridine (10 mL) was stirred for 0.5 hour in an ice bath and 4 hours at room temperature. Concentration of the reaction mixture and flash chromatography gave (25R)-3,-(tert-butyldimethylsilyloxy)-4,4-dimethylcholest-5,7-dien-26-tosylate (0.57 g).

Melting point: 68° C. The $^1$H-NMR spectrum (CDCl$_3$, d) showed characteristic signals at: 0.02 (d, 12H), 0.52 (s, 3H), 0.90 (s, 18H), 2.40 (s, 3H, ArCH$_3$), 3.30 (m, 1H, H-3), 3.80 (m, 2H, H-26), 5.52 (m, 1H, H-6), 5.85 (d, 1H, H-7), 7.30 (d, 2H, aryl), 7.74 (d, 2H, aryl). The $^{13}$C-NMR spectrum (CDCl$_3$, d) showed characteristic signals at: 47.5 (C-9), 54.7 (C14), 56.0 (C-17), 75.6 (C-26), 78.0 (C-3), 118.0 (C-6), 119.2 (C-7), 128.3 (C-ortho), 130.2 (C-meta), 133.6 (C-para), 141.5 (C-8), 144.9 (C-ipso), 151.3 (C-5). The mass spectrum showed characteristic peaks at: 696.4 (M$^+$).

Step 2.

A solution of (25R)-3β-(tert-butyldimethylsilyloxy)-4,4-dimethylcholest-5,7-dien-26-toluene sulphonate (0.57 g, 0.82 mmol) and lithium chloride (300 g, 7 mmol) in dimethylformamide was heated at 50° C. for 2 hours. Addition of water (30 mL), ether extraction and chromatography gave of (25R)-3β-(tert-butyldimethylsilyloxy)-4,4-dimethyl-26-chloro-cholest-5,7-diene (424 mg).

Melting point: 114.5–116° C. The $^1$H-NMR spectrum (CDCl$_3$, d) showed characteristic signals at: 0.02 (d, 12H), 0.52 (s, 3H), 0.90 (s, 18H), 1.04 (s, 3H), 1.08 (s, 3H), 3.35 (m, 3H, H-3 and H-26), 5.50 (m, 1H, H-6), 5.83 (d, 1H, H-7). The $^{13}$C-NMR spectrum (CDCl$_3$, d) showed characteristic signals at: 77.4 (C-3), 117.7 (C-6), 118.9 (C-7), 141.1 (C-8), 150.8 (C-5). The mass spectrum showed characteristic peaks at: 560.4 (M$^+$).

Step 3.

A mixture of (25R)-3β-(tert-butyldimethylsilyloxy)-4,4-dimethyl-26-chlorocholest-3,7-diene (380 mg, 0.67 mmol), concentrated HCl (5 mL), benzene (6 mL) and ethanol (25 mL) was heated at reflux for 5 hours. The reaction mixture was concentrated to half the volume and water (30 mL) was added. Extraction with dichloromethane, drying over magnesium sulphate and removal of solvent under reduced pressure gave a residue which was crystallized 3 times from hexane to give (25R)-26-Chloro-4,4-dimethyl-5α-cholesta-8,14-dien-3β-ol (0.135 g).

Melting point: 145–145.5° C. The $^1$H-NMR spectrum (CDCl$_3$, d) showed characteristic signals at: 0.80 (s, 3H), 0.82 (s, 3H), 0.92 (s, 3H), 0.94 (s, 3H), 0.99 (s, 3H), 1.01 (s, 3H), 1.03 (s, 3H), 3.24 (m, 1H, H-3), 3.42 (m, 2H, H-26), 5.33 (m, 1H, H-15). The $^{13}$C-NMR spectrum (CDCl$_3$, d) showed characteristic signals at: 57.6 (C-26), 79.4 (C-3), 117.7 (C-15), 123.2 (C-14), 142.1 (C-9), 151.4 (C-8). The mass spectrum showed characteristic peaks at: 446.3 (M$^+$). Elemental analysis:

| Calculated | C 77.90 | H 10.59 | Cl 7.93 |
| Found | C 77.85 | H 11.07 | Cl 8.05 |

Example 23

(25R)-26-Iodo-4,4-dimethyl-5α-cholesta-8,14-dien-3β-ol

A mixture of (25R)-26-chloro-4,4-dimethyl-5α-cholesta-8,14-dien-3β-ol (50 mg, 0.1 mmol) and sodium iodide (0.8 g) in acetone (3 mL) were heated at 55° C. in a sealed reaction vessel for 3 days. Addition of water, extraction with diethyl ether and concentration under reduced pressure gave a residue which was crystallised 3 times from hexane to give the title compound (37 mg).

Melting point: 148° C. The $^1$H-NMR spectrum (CDCl$_3$, d) showed characteristic signals at: 0.80 (s, 3H), 0.82 (s, 3H), 1.01 (s, 3H), 1.02 (s, 3H), 3.20 (m, 3H, H-26 and H-3), 5.33 (m, 1H, H-15). The mass spectrum showed characteristic peaks at: 538.3 (M$^+$).

Example 24
3β-Hydroxycholest-5-en-16-one

To a solution of cholest-5-ene-3β,16β-diol (700 mg, 1.7 mmol) and sodium acetate (trihydrate) 4.6 g, 34 mmol) in glacial acetic acid (85 mL) was added dropwise, a solution of chromium trioxide in water (1.7 mL) and acetic acid (0.8 mL). After stirring for 16 hours, methanol (5mL) was added and the reaction mixture concentrated at reduced pressure. Water was added and the aqueous phase extracted using dichloromethane. Drying over magnesium sulphate, concentration and purification by flash chromatography gave the title compound (560 mg).

The $^1$H-NMR spectrum (CDCl$_3$, d) showed characteristic signals at: 0.82 (s, 3H), 0.83 (s, 3H), 0.86 (s, 3H), 0.97 (d, 3H), 1.03 (s, 3H), 3.50 (m, 1H, H-3), 5.35 (m, 1H, H-6). The $^{13}$C-NMR spectrum (CDCl$_3$, d) showed characteristic signals at: 72.0 (C-3), 121.4 (C-6), 141.4 (C-5), 218.0 (C-16). The mass spectrum showed characteristic peaks at: 400.4 (M$^+$).

Example 25
Cholestan-3β,16β-diol

Cholest-5-ene-3β,16β-diol (600 mg, 1.4 mmol) in ethyl acetate (15 mL) was hydrogenated at atmospheric pressure over 5% palladium on carbon for 3 days. Removal of catalyst by filtration through Celite and purification of the residue by flash chromatography gave the title compound (190 mg). The $^1$H-NMR spectrum (CDCl$_3$, d) showed characteristic signals at: 0.81 (s, 3H), 0.86 (s, 3H), 0.89 (s, 3H), 3.55 (m, 1H, H-3), 4.31 (m, 1H, H-16). The $^{13}$C-NMR spectrum (CDCl$_3$, d) showed characteristic signals at: 71.7 (C-3), 72.9 (C-8). The mass spectrum showed characteristic peaks at: 404.4 (M$^+$).

Example 26
4,4-Dimethylcholest-5-en-16-ol-3-one

Step 1.

To a solution of cholest-5-ene-3β,16β-diol-3-benzoate (6.1 g, 12 mmol), (prepared as described in Bioorg. Med. Chem. Lett. 1995, 3, 367–374.) in dichloromethane (50 mL) at ice bath temperature was added tert-butyldimethylsilyl triflate (20 mmol) and the solution stirred 0.5 hour. Water was added and the aqueous phase extracted with dichloromethane. Removal of solvent under reduced pressure and purification of the residue by recrystallization from methanol gave 16β-(tert-butyldimethylsilyloxy)cholest-5-en-3β-yl benzoate (8.1 g).

The $^1$H-NMR spectrum (CDCl$_3$, d) showed characteristic signals at: 0.01 (s, 3H), 0.02 (3H, s), 4.25 (m, 1H, H-16), 4.75 (m, H-3), 5.42 (d, 1H, H-6), 7.4 (m, 3H, aryl), 8.2 (m, 2H, aryl). The mass spectrum showed characteristic peaks at: 621.6 (M$^+$).

Step 2.

To a suspension of lithium aluminium hydride (4.5 g, 120 mmol) in diethyl ether (700 mL) was added, dropwise 16β-(tert-butyldimethylsilyloxy)cholest-5-en-3β-yl benzoate (8.1 g, 12 mmol) in diethyl ether (50 mL). After stirring at room temperature for 15 minutes and at 40° C. for 0.5 hour, water was added. The inorganic impurities were removed by filtration through Celite, and after removal of solvent under reduced pressure the residue was purified by flash chromatography to give 16β-(tert-butyldimethylsilyloxy)cholest-5-en-3β-ol (6.7 g).

The 1H-NMR spectrum (CDCl$_3$, d) showed characteristic signals at: 0.01 (s, 3H), 0.02 (3H, s), 3.49 (m, H-3), 4.25 (m, 1H, H-16), 5.32 (s, 1H, H-6).

Step 3.

A mixture of 16β-(tert-butyldimethylsilyloxy)cholest-5-en-3β-ol (6.7 g, 12 mmol) and 1-methylpiperidone (25 mL) in toluene (500 mL) was heated to reflux temperature and 50 ml toluene was distilled off. Aluminium triisopropyl oxide (9.8 g, 48 mmol) in toluene (50 mL) was then added dropwise and the whole heated at reflux for 4 hours. After cooling, water (200 mL) was added and the aqueous layer separated and extracted with diethyl ether. The combined organic layers were washed with water (100 mL), dried over magnesium sulphate and concentrated to give residue which was purified by recrystallization from methanol to give 16β-(tert-butyldimethylsilyloxy)cholest-4-en-3-one (5.4 g).

The $^1$H-NMR spectrum (CDCl$_3$, d) showed characteristic signals at: 0.01 (s, 3H), 0.02 (3H, s), 4.26 (m, 1H, H-16), 5.68 (s, 1H, H-4). The $^{13}$C-NMR spectrum (CDCl$_3$, d) showed characteristic signals at: 72.1 (C-16), 123.8 (C-4), 171.5 (C-5), 199.6 (C-3). The mass spectrum showed characteristic peaks at: 515.5 (M$^+$).

Step 4.

To a stirred suspension of KOtBu (5.6 g, 50 mmol) in tBuOH (150 ml) at 45° C. was added 16β-(tert-butyldimethylsilyloxy)cholest-4-en-3-one (5.2 g, 10 mmol) in THF (15 mL) and the whole stirred for 20 minutes. Iodomethane (6.2 ml) was added and the reaction stirred a further 0.5 hour, concentrated to one-half the original volume and poured into 200 mL ice water. Extraction with ethyl acetate, drying over magnesium sulphate and concentration gave a residue which was purified by recrystallization from methanol to give 4,4-dimethyl-16,-(tert-butyldimethylsilyloxy)cholest-4-en-3-one (4.0 g).

The $^1$H-NMR spectrum (CDCl$_3$, d) showed characteristic signals at: 0.01 (s, 3H), 0.02 (3H, s), 2.50 (m, 2H, H-2), 4.30 (m, 1H, H-16), 5.54 (m, 1H, H-6). The $^{13}$C-NMR spectrum (CDCl$_3$, d) showed characteristic signals at: 72.3 (C-16), 119.7 (C-6), 150.0 (C-5), 216.0 (C-3). The mass spectrum showed characteristic peaks at: 543.5 (M$^+$).

Step 5.

A mixture of 4,4-dimethyl-16β-(tert-butyldimethylsilyloxy)cholest-5-en-3-one (40 mg, 0.07 mmol), concentrated HCl (0.2 mL) and ethanol (5 mL) were heated to reflux for 20 hours. Removal of solvent under reduced pressure and recrystallization twice from methanol gave 4,4-dimethylcholest-5-en-16-ol-3-one (20 mg).

The $^1$H-NMR spectrum (CDCl$_3$, d) showed characteristic signals at: 0.87 (s, 3H), 0.88 (s, 3H), 0.91 (s, 3H), 0.99 (d, 3H), 1.20 (s, 3H), 1.21 (s, 3H), 4.45 (m, 1H, H-16), 5.55 (m, 1H, H-6). The $^{13}$C-NMR spectrum (CDCl$_3$, d) showed characteristic signals at: 119.7 (C-6), 149.9 (C-5), 216.7 (C-3). The mass spectrum showed characteristic peaks at: 428.4 (M$^+$).

Example 27
Cholest-5-ene-4,4-dimethyl-3β,16β-diol

Step 1.

To a suspension of lithium aluminium hydride (570 mg, 15 mmol) in diethyl ether (200 mL) was added 4,4-dimethyl-16β-(tert-butyldimethylsilyloxy)cholest-4-en-3-one (2.8 g, 15 mmol) in 20 mL ether and the whole was stirred for 1.5 hour. Water was added and the solution filtered through a plug of Celite. Extraction with ether and concentration under reduced pressure gave a residue that was purified by crystallization from methanol to give 3-hydroxy-4,4-dimethyl-16β-(tert-butyldimethylsilyloxy)cholest-4-ene (400 mg).

The $^1$H-NMR spectrum (CDCl$_3$, d) showed characteristic signals at: 0.01 (s, 3H), 0.02 (s, 3H), 1.07 (d, 3H), 1.08 (s, 3H), 1.16 (s, 3H), 3.21 (m, 1H, H-3), 4.25 (m, 1H, H-16), 5.51 (m, 1H, H-6). The $^{13}$C-NMR spectrum (CDCl$_3$, d) showed characteristic signals at: 72.8 (C-16), 77.9 (C-3), 120.3 (C-6), 150.4 (C-5). The mass spectrum showed characteristic peaks at: 545.5 (M$^+$).

Step 2.

A mixture of 3-hydroxy-4,4-dimethyl-16β-(tert-butyldimethylsilyloxy)-cholest-4-ene (1.1 g, 2 mmol), concentrated HCl (2.5 mL) and ethanol (25 mL) was heated to reflux for 2 days. The mixture was concentrated under reduced pressure and water was added. The aqueous phase was extracted with ethyl acetate, and the combined organic phases washed with sodium bicarbonate and water. Concentration under reduced pressure gave a residue which was purified by flash chromatography to give cholest-5-ene-4,4-dimethyl-3β,16β-diol (225 mg).

The $^1$H-NMR spectrum (CDCl$_3$, d) showed characteristic signals at: 0.86 (s, 3H), 0.87 (s, 3H), 0.95 (d, 3H), 1.07 (d, 3H), 1.08 (s, 3H), 1.16 (s, 3H), 3.21 (m, 1H, H-3), 4.31 (m, 1H, H-16), 5.51 (m, 1H, H-6). The $^{13}$C-NMR spectrum (CDCl$_3$, d) showed characteristic signals at: 77.0 (C-3), 119.4 (C-6), 149.4 (C-S). The mass spectrum showed characteristic peaks at: 430.4 (M$^+$).

Example 28

4,4-Dimethylcholest-5,7-dien-3β,16β-diol

Step 1.

A mixture of 3β-hydroxy-4,4-dimethyl-16β-(tert-butyldimethylsilyloxy)cholest-4-ene (4.0 g, 7.3 mmol), tert-butyldimethylsilylchloride (5.5 g, 35 mmol) and imidazole (10.0 g, 146 mmol) in DMF (250 mL) were heated for 7 hours at 70° C., poured into water (250 mL) and extracted with diethyl ether.

Concentration under reduced pressure and crystallization from methanol gave 3β–16β-bis(tert-butyldimethylsilyloxy)-4,4-dimethylcholest-5-ene (4.3 g).

The $^1$H-NMR spectrum (CDCl$_3$, d) showed characteristic signals at: 0.02 (m, 12H), 0.83 (s, 3H), 3.20 (m, 1H, H-3), 4.32 (m, 1H, H-16), 5.52 (m, 1H, H-6). The $^{13}$C-NMR spectrum (CDCl$_3$, d) showed characteristic signals at: 72.4 (C-16), 78.0 (C-3), 119.5 (C-6), 150.5 (C-5). The mass spectrum showed characteristic peaks at: 659.7 (M$^+$).

Step 2.

A mixture of 3β–16β-bis(tert-butyldimethylsilyloxy)-4,4-dimethylcholest-5-ene (500 mg, 0.75 mmol) and 1,3-dibromo-5,5-dimethylhydantoin (140 mg, 0.5 mmol) in benzene (15 mL) and hexane (35 mL) was heated at reflux temperature for 1 hour. After cooling, the solid material was removed by filtration and the organic phase concentrated under reduced pressure. Quinaldine (1 mL) and o-xylene (25 mL) was added and the whole heated at 140° C. for 1 hour. Concentration of the reaction mixture and chromatography gave 3β,16β-bis(tert-butyldimethylsilyloxy)-4,4-dimethylcholesta-5,7-diene (310 mg).

The $^1$H-NMR spectrum (CDCl$_3$, d) showed characteristic signals at: 0.02 (m, 12H), 0.83 (s, 3H), 1.05 (d, 3H), 1.07 (s, 3H), 3.30 (m, 1H, H-3), 4.35 (m, 1H, H-16), 5.50 (m, 1H, H-6), 5.85 (m, H-7). The $^{13}$C-NMR spectrum (CDCl$_3$, d) showed characteristic signals at: 72.7 (C-16), 77.7 (C-3), 114.0 (C-6), 17.9 (C-7), 140.9 (C-8), 154.2 (C-5). The mass spectrum showed characteristic peaks at: 656.5 (M$^+$).

Step 3.

A mixture of 3 p, 16,-bis(tert-butyldimethylsilyloxy)-4,4-dimethylcholesta-5,7-diene (110 mg, 0.2 mmol) and DIBAL (8 mL of 1.0 M in hexanes) was heated to reflux for 3 days. Water was added and the aqueous phase extracted with dichloromethane and the organic phase filtered through Celite and concentrated to give a residue which was purified by flash chromatography to give 4,4-dimethylcholest-5,7-dien-3β,16β-diol (33 mg).

Melting point: 171–173° C. The $^1$H-NMR spectrum (CDCl$_3$, d) showed characteristic signals at: 0.80 (s, 3H), 0.84 (s, 3H), 0.87 (s, 3H), 3.24 (m, 1H, H-3), 3.42 (m, 2H, H-26), 4.45 (m, 1H, H-16), 5.52 (1H, m, H-6), 5.95 (d, 1H, H-7). The $^{13}$C-NMR spectrum (CDCl$_3$, d) showed characteristic signals at: 72.2 (C-16), 117.3 (C-8), 118.8 (C-7), 139.9 (C-6), 150.1 (C-5). The mass spectrum showed characteristic peaks at: 428.3 (M$^+$).

Example 29

4,4-Dimethyl-5a-cholesta-8,14-diene-3β,16β-diol.

A mixture of 4,4-dimethylcholest-5,7-dien-3 p, 16,-diol (65 mg, 0.15 mmol), concentrated HCl (0.35 mL), benzene (0.35 mL) and ethanol (4 mL) was heated to reflux for 4 hours. Concentration of the reaction mixture under reduced pressure and crystallization of the residue from methanol gave the title compound (5 mg). The $^1$H-NMR spectrum (CDCl$_3$, d) showed characteristic signals at: 3.42 (m, 1H, H-3), 5.95 (d, 1H, H-15).

Example 30

4,4-Dimethylcholest-5-en-3,16-dione

To a mixture of cholest-5-ene-4,4-dimethyl-3β,16β-diol (43 mg, 0.1 mmol), sodium acetate (340 mg, 2.5 mmol) and glacial acetic acid (4 mL) was added chromium trioxide (33 mg, 0.3 mmol) in water (0.3 mL) and acetic acid (0.2 mL) and the mixture stirred for 18 hours. Methanol (2 mL) was added and the reaction mixture concentrated at reduced pressure. Water was added and the aqueous phase extracted using dichloromethane. Drying over magnesium sulphate, concentration and purification by flash chromatography gave the title compound (40 mg).

The $^1$H-NMR spectrum (CDCl$_3$, d) showed characteristic signals at: 0.80 (s, 3H), 0.84 (s, 3H), 0.92 (d, 3H), 5.56 (m, 1H, H-6). The $^{13}$C-NMR spectrum (CDCl$_3$, d) showed characteristic signals at: 119.7 (C-6), 150.5 (C-5), 216.8 (C-3), 218.9 (C-16). The mass spectrum showed characteristic peaks at: 426.2 (M$^+$).

Example 31

Cholesta-5,16-dien-3-one

To a stirred suspension of KOtBu (900 mg, 8.2 mmol) in tBuOH (25 mL) at 45° C. was added cholesta-4,16-dien-3-one (620 mg, 1.6 mmol) in THF (5 mL) and the whole stirred for 20 minutes. Iodomethane (1 ml) was added and the reaction stirred a further 12 hours., concentrated to one half the original volume and poured into 20 mL ice water. Extraction with ethyl acetate, drying over magnesium sulphate and concentration gave a residue which was purified by flash chromatography to give the title compound (220 mg).

The $^1$H-NMR spectrum (CDCl$_3$, d) showed characteristic signals at: 0.81 (s, 3H), 0.85 (s, 3H), 0.87 (s, 3H), 0.89 (s, 3H), 0.95 (d, 3H), 5.30 (s, H-16), 5.57 (m, 1H, H-6).

Example 32

3β-Hydroxy-4,4-dimethylcholest-5,16-diene

To a suspension of lithium aluminium hydride (80 mg, 2 mmol) in diethyl ether (15 mL) was added 4,4-dimethylcholesta-5,16-dien-3-one (220 mg, 0.5 mmol) in 10 mL ether and the whole was stirred for 1.5 hours. Water was added and the solution filtered through a plug of Celite. The aqueous phase was extracted with ether, washed with 4N HCl, brine, dried over magnesium sulphate and concentrated under reduced pressure to give 3β-hydroxy-4,4-dimethylcholesta-5,16-diene (220 mg).

The $^1$H-NMR spectrum (CDCl$_3$, d) showed characteristic signals at: 0.79 (s, 3H), 0.83 (s, 3H), 0.85 (s, 3H), 0.95 (d, 3H), 1.03 (s, 3H), 1.07 (s, 3H), 1.12 (s, 3H), 3.20 (m, 1H, H-3), 5.30 (s, H-16), 5.57 (m, 1H, H-6).

Example 33

4,4-Dimethylcholest-5-en-3β,17α-diol

Step 1.

To a solution of 3βhydroxy-4,4-dimethylcholesta-5,16-diene (220 mg, 0.5 mmol) in pyridine (1.5 mL) at ice bath temperature was added benzoyl chloride (0.1 mL) and the whole stirred for 1.5 hours. Concentration under reduced pressure and purification of the residue by flash chromatography gave 3β-benzoyloxy-4,4-dimethylcholesta-5,16-diene (300 mg).

The $^1$H-NMR spectrum (CDCl$_3$, d) showed characteristic signals at: 4.74 (m, 1H, H-3), 5.30 (s, 1H, H-16), 5.61 (m, 1H, H-6), 7.50 (m, 3H, aryl), 8.07 (d, 2H, aryl).

Step 2.

To a solution of 3β-benzoyloxy-4,4dimethylcholesta-5,16-diene (250 mg, 4.8 mmol) in dichloromethane (5 mL) at ice bath temperature was added mCPBA (180 mg, 5.2 mmol) and the whole stirred for 3 hours. 2N NaOH (5 mL) was added and the aqueous phase extracted with dichloromethane. Concentration under reduced pressure gave a residue which was tritured with methanol and purified by flash chromatography to give 3β-benzoyloxy-4,4-dimethyl-16α-epoxycholesta-5-ene (50 mg).

The $^1$H-NMR spectrum (CDCl$_3$, d) showed characteristic signals at: 3.24 (s, 1H, H-16), 4.71 (m, 1H, H-3), 5.60 (m, 1H, H-6). 7.50 (m, 3H, aryl), 8.07 (d, 2H, aryl).

Step 3.

3β-benzoyloxy-4,4-dimethyl-16α-epoxycholesta-5-ene (40 mg, 0.075 mmol) in THF (1 mL) was added to a suspension of lithium aluminium hydride (50 mg, 1.3 mmol) in THF (3mL) and the whole heated to reflux temperature for 6 hours. Diethyl ether (50 mL) and 4N NaOH (0.2 mL) was added and the resultant precipitate collected by filtration and washed with ether. Purification by flash chromatography gave the title compound 4,4-dimethyl-cholest-5-en-3,17α-diol (12 mg).

The $^1$H-NMR spectrum (CDCl$_3$, d) showed characteristic signals at: 0.78 (s, 3H), 0.85 (s, 3H), 0.87 (s, 3H), 0.90 (s, 3H), 1.05 (s, 3H), 1.07 (s, 3H), 1.12 (s, 3H), 3.23 (m, 1H, H-3), 5.56 (m, 1H, H-6). The $^1$C-NMR spectrum (CDCl$_3$, d) showed characteristic signals at: 86.8 (C-17), 120.5 (C-6), 149.0 (C-5). The mass spectrum showed characteristic peaks at: 430.3 (M$^+$).

Examples 34–36

(25R)-Cholest-5-ene-3β,16β-,26-triol, (25R)-3β,26-Dihydroxycholest-5-en-16-one, (25R)-Cholest-5-ene-3β,26-diol Prepared according to the procedure described by Arunachalam et al, J. Org. Chem. 1981, 46, 2966–2968.

Examples 37–38

Cholest-5-ene-3β,16β-diol, Cholest-5-ene-3β,16β-diol 3-benzoate

The above two compounds were prepared as described by Kim in Bioorg. Med. Chem. 1995, 3, 367–374.

Example 39

4,4-Dimethylcholest-8-en-3β,15α-diol

Prepared analogously to general method described by Dolle et al. in J. Chem. Soc. Chem. Comm. 1988, 19.

Example 40

4,4-dimethyl-5α-cholesta-8,14,24-trien-3-one

Step 1.

A suspension of 4,4-dimethyl-5α-chola-8,14-dien-3β,24-diol (500 mg, 1.29 mmol), N-methylmorpholine-N-oxide (600 mg, 5.2 mmol), TPAP (45 mg, 0.13 mmol) and crushed molecular sieves (2 g) in dichloromethane (5 mL) was stirred for 30 minutes at room temperature. Addition of ether (15 mL) and filtration through kieselguhr gave a dark brown solution which was concentrated under reduced pressure and purified by chromatography (Eluant: 3 hexane: 1 ethyl acetate) to give the 3-oxo-4,4-dimethyl-5α-chola-8,14-dien-24-aldehyde (345 mg, 70%) as a white solid with melting point 96.5–97° C.

$^1$H NMR (CDCl$_3$, 300 MHz); 5.40 (1H, s, H-15), 1.10 and 1.04 (3H each, s, CH$_3$-4a and 18), 0.93 (3H, d, J=6Hz, CH$_3$-20), 0.82 (6H, s, CH$_3$-4b and 19), 2.6–0.8 (m, remaining H).

Step 2.

A solution of isopropyltriphenylphosphorane was prepared by addition of BuLi (0.16 ml of 1.6M in hexanes, 0.26 mmol) to a suspension of isopropyltriphenylphosphonium bromide (98 mg, 0.26 mmol) in THF (2 mL) at ice bath temperature. The corresponding deep red phosphorane solution was stirred a further 0.5 hour and then added dropwise via syringe to a solution of 3-oxo-4,4-dimethyl-5α-chola-8,14-dien-24-aldehyde (71 mg, 0.18 mmol) in THF (2ml) at −78° C. and stirred 2 hours before slowly warming to room temperature and stirring overnight. Saturated ammonium chloride (3 mL) was added and the aqueous phase extracted using diethyl ether, and the organic phase dried over anhydrous sodium sulphate. Flash chromatography (Eluant: 6 hexane: 1 ethyl acetate) gave the title compound (38 mg, 50%).

$^1$H NMR (CDCl$_3$, 300 MHz); 5.40 (1H, s, H-15), 5.10 (1H, t, J=6 Hz, H-24), 1.67 and 1.60 (3H each, s, CH$_3$-26 and 27), 1.04 and 1.02 (3H each, s, CH$_3$-4a and 18), 0.95 (3H, d, J=6 Hz, CH$_3$-20), 0.83 (6H, s, CH$_3$-4b and 19), 2.6–0.8 (m, remaining H).

Example 41

Treatment of Infertility with the Use of a MAS Agonist in vitro

Eggs are retrieved by ultrasound guided transvaginal aspiration from the ovary of an either hormone stimulated or un-stimulated female patient. The hormone stimulation may the standard long IVF protocol comprising using down regulation with Gonatropin antagonist e.g. Synarella nose-spray followed after 14 days by FSH daily injection (Gonal-F given SC)150 IU daily. 36 hours before egg collection the patient is given hCG (10.000 IU human chorion gonadotropin, SC) to induce final maturation of follicle and oocyte.

The compound is added to culture media in 3 uM concentration and allowed to interact with the gamete prior to fertilization either to mediate or to improve the process of meiotic maturation. The oocytes are fertilised in vitro, cultured in vitro and back-transferred to the patient uterus typically on day 3 after oocyte collection.

Example 42

Treatment of Female Infertility with the Use of a MAS Agonist in vivo

The compound is administrated orally twice daily in a dose of 10 mg/kg to the female patient from day at the time of final oocyte maturation induced by injection of hCG (10.000 IU human chorion gonadotropin, SC). The hCG can be given in a normal cycle, the cycle can be induced by with-drawal of progesterone administrated minimum 10 days prior to withdrawal to induce bleeding and cyclic activity in patient with amenorrhoea or PCO's (polycystic ovarian syndrome) or the hCG can be given as a integrated part of normal long-hormone stimulation in an IVF protocol (using down regulation with Gonatropin antagonist e.g. Synarella nose-spray followed after 14 days by FSH daily injection 150–225 IU daily.

The patient receives the treatment either as an add-on to normal IVF treatment with egg collection, IVF and embryo transfer or alternatively the treatment is used in combination with fertilization obtained using insemination or natural intercourse.

The treatment will elevate the patient's serum level of MAS agonists immediately close to ovulation whereby an improved oocyte maturation quality is obtained. The ovulated egg quality is improved by the meiosis induction of the daily administrated compound.

Example 43

Treatment of Male Infertility with the Use of a MAS Agonist in vivo

The compound is administrated orally twice daily in a dose of 10 mg/kg to the male patient consecutive for at least 60 (sixty) days. The treatment will elevate the patient's serum level of MAS agonists, which will positively stimulate the processes of meiosis in the testis and consequently over time the semen quality parameters. The patients semen quality parameters (number of spermatozoa, morphology, progressive motility etc) will individually or combined be improved.

Example 44

Treatment Regimen for Female Contraception Using a MAS Agonist and Premature Oocyte Maturation The compound is administered orally twice daily in a dose of 50 mg/kg to the female patient every day throughout the normal cycle. The patient receives the treatment either as an add-on to normal IVF treatment with egg collection, IVF and embryo transfer or alternatively the treatment is used in combination with fertilization obtained using insemination or natural intercourse.

The treatment will elevate the patient's serum level of MAS agonists long before ovulation will occur and mediate oocyte maturation long before ovulation. When ovulated, the resulting overmature oocytes is no longer viable or able to be fertilized. The normal menstrual cycle is not to be affected, nor is the normal level and dynamics of steroid hormones altered.

Example 45

Treatment Regimen for Female Contraception Using a MAS Antagonist Blocking the Process of Meiosis in Ovaries The compound is administered orally twice daily in a dose of 50 mg/kg to the female individual every day throughout the normal cycle. The treatment will elevate the subject's serum level of MAS antagonists, which will effectively inhibit the natural oocyte maturation to occur. The process of ovulation will occur normally and the cyclic activity remains un-altered however at the time of ovulation a meiosis arrested and thus immature and un-fertilizable oocyte will be ovulated. The normal levels and dynamics of steroid hormones remain un-affected as well as the natural cyclic activity and monthly menses remains un-affected.

Example 46

Treatment Regimen for Male Contraception Using a MAS Antagonist Blocking the Process of Meiosis in Testis.

The compound is administered orally twice daily in a dose of 50 mg/kg to the male individual every day consecutively for a minimum of 60 days. The process of spermatogenesis takes approximately 60–65 days in the human male. The treatment will induce a level of MAS antagonists in the treated subjects serum, which will effectively inhibit the natural meiotic process and specialization that leads to the formation of fertilizing mature spermatozoa in the subject's testis. The process of spermatogenesis will be inhibited and exclusively non-fertilizing spermatozoa will be produced and released, however the endocrinology of the testis is unaffected and the normal levels and dynamics of steroid hormones remains unaltered.

What is claimed is:

1. A method of regulating meiosis in a mammalian germ cell comprising administering to a germ cell in need of such regulation, an effective amount of a compound of formula (I)

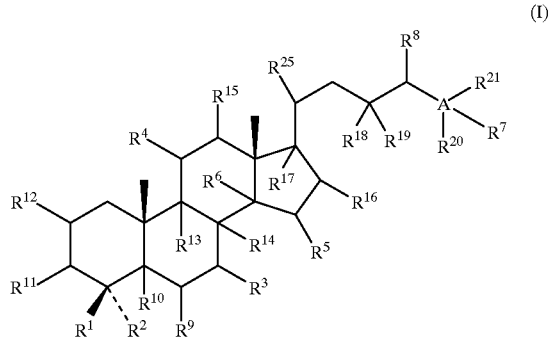

wherein $R^1$ and $R^2$, independently, are selected from the group consisting of hydrogen and branched or unbranched $C_1$–$C_6$ alkyl which may be substituted by halogen, hydroxy or cyano, or wherein $R^1$ and $R^2$ together designate methylene or, together with the carbon atom to which they are bound, form a cyclopropane ring, a cyclopentane ring, or a cyclohexane ring; $R^3$ is selected from the group consisting of hydrogen, methylene, hydroxy, methoxy, acetoxy, oxo, $=NOR^{26}$ wherein $R^{26}$ is hydrogen or $C_1$–$C_3$ alkyl, halogen, and $C_1$–$C_4$ alkyl; $R^4$ is selected from the group consisting of hydrogen, methylene, hydroxy, methoxy, acetoxy, oxo, $=NOR^{27}$ wherein $R^{27}$ is hydrogen or $C_1$–$C_3$ alkyl, halogen, and $C_1$–$C_4$ alkyl; $R^5$ designates, together with $R^6$, an additional bond between the carbon atoms to which $R^5$ and $R^6$ are bound; $R^9$ is hydrogen; $R^{10}$ is hydrogen; $R^{11}$ is selected from the group consisting of hydroxy, alkoxy, substituted alkoxy, alkanoyloxyalkyl, acyloxy, sulphonyloxy, phosphonyloxy, oxo, $=NOR^{28}$ wherein $R^{28}$ is hydrogen or $C_1$–$C_3$ alkyl, halogen and $C_1$–$C_4$ alkyl; $R^{12}$ is selected from the group consisting of hydrogen, $C_1$–$C_3$ alkyl, vinyl, $C_1$–$C_3$ alkoxy and halogen; $R^{13}$ designates, together with $R^{14}$, an additional bond between the carbon atoms to which $R^{13}$ and $R^{14}$ are bound; $R^{15}$ is selected from the group consisting of hydrogen, $C_1$–$C_4$ alkyl, methylene, hydroxy, methoxy, acetoxy, oxo, and $=NOR^{23}$ wherein $R^{23}$ is hydrogen or $C_1$–$C_3$ alkyl; $R^{16}$ is selected from the group consisting of hydrogen, $C_1$–$C_3$ alkyl, methylene, hydroxy, methoxy, oxo and $=NOR^{24}$ wherein $R^{24}$ is hydrogen or $C_1$–$C_3$ alkyl; $R^{17}$ is hydrogen or hydroxy; $R^{18}$ and $R^{19}$ are, independently, hydrogen or fluoro; $R^{25}$ is selected from the group consisting of hydrogen, $C_{1-4}$ alkyl, methylene, hydroxy and oxo; A is a carbon atom; $R^7$ is selected from the group consisting of hydrogen, hydroxy and fluoro, and $R^8$ is selected from the group consisting of hydrogen, $C_1$–$C_4$ alkyl, methylene and halogen; $R^{20}$ is selected from the group consisting of $C_1$–$C_4$ alkyl, trifluoromethyl and $C_3$–$C_6$ cycloalkyl and $R^{21}$ is selected from the group consisitning of $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl; provided that the compound of formula (I) does not have any cumulated double bonds and further provided that the compound is not one of the following compounds:

Cholesta-8,14-diene-3β-ol;
4-Methylcholesta-8,14-diene-3β-ol;
4-Ethylcholesta-8,14-diene-3β-ol;
4,4-Dimethylcholesta-8,14-diene-3β-ol;
4α-Methyl-4β-ethylcholesta-8,14-diene-3β-ol;
4α-Ethyl-4β-methylcholesta-8,14-diene-3β-ol;
4,4-Diethylcholesta-8,14-diene-3β-ol;
4-Propylcholesta-8,14-diene-3β-ol;

4-Butylcholesta-8,14-diene-3β-ol;
4-Isobutylcholesta-8,14-diene-3β-ol;
4,4-Tetramethylenecholesta-8,14-diene-3β-ol; and
4,4-Pentamethylenecholesta-8,14-diene-3β-ol;
or esters or ethers thereof.

2. The method of claim 1, provided that it is not a compound of formula (II)

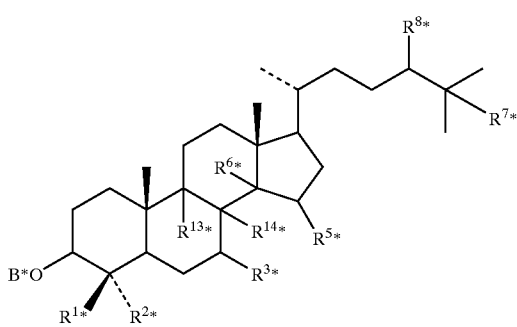

(II)

wherein $R^{1*}$ and $R^{2*}$, independently, are selected from the group consisting of hydrogen, branched or unbranched $C_1$–$C_6$ alkyl which may be substituted by halogen or hydroxy or wherein $R^{1*}$ and $R^{2*}$, together with the carbon atom to which they are bound, form a cyclopentane ring or a cyclohexane ring; $R^{13*}$ and $R^{14*}$ together designate an additional bond between the carbon atoms to which they are bound in which case $R^{3*}$ is hydrogen and $R^{6*}$ and $R^{5*}$ together designate an additional bond between the carbon atoms to which they are bound.

3. The method of claim 1, wherein $R^1$ and $R^2$ are both hydrogen; both methyl; one is hydrogen and the other is methyl; or together designate methylene, or wherein $R^1$ and $R^2$, together with the carbon atom to which they are bound, form a cyclopropane ring, a cyclopentane ring, or a cyclohexane ring.

4. The method of claim 1, wherein $R^1$ is branched or unbranched $C_1$–$C_6$ alkyl, optionally substituted by halogen, hydroxy or cyano, and wherein $R^2$ is branched or unbranched $C_1$–$C_6$ alkyl, optionally substituted by halogen, hydroxy or cyano.

5. The method of claim 1, wherein $R^{11}$ is hydroxy, alkoxy, aralkyloxy, alkoxyalkoxy or alkanoyloxyalkyl, each group comprising a total of up to 10 carbon atoms, $C_1$–$C_4$ alkoxy, methoxy, ethoxy, $CH_3OCH_2O$— pivaloyloxymethoxy, an acyloxy group derived from an acid having from 1 to 20 carbon atoms, an acyloxy group selected from the group consisting of acetoxy, benzoyloxy, pivaloyloxy, butyryloxy, nicotinoyloxy, isonicotinoyloxy, hemi succinoyloxy, hemi glutaroyloxy, butylcarbamoyloxy, phenylcarbamoyloxy, butoxycarbonyloxy, tert-butoxycarbonyloxy and ethoxycarbonyloxy.

6. The method of claim 1, wherein $R^{11}$ is sulphonyloxy, phosphonyloxy, oxo, =NOH, =$NOR^{28}$, wherein $R^{28}$ is $C_1$–$C_3$ alkyl, or wherein $R^{11}$ is halogen, hydroxy or $C_1$–$C_4$ alkyl.

7. The method of claim 1, wherein $R^{12}$ is hydrogen, $C_1$–$C_3$ alkyl, $C_1$–$C_3$ alkoxy, or halogen.

8. The method of claim 1, wherein the germ cell is an oocyte.

9. The method of claim 8, wherein the compound is administered to an oocyte ex vivo.

10. The method of claim 8, wherein the germ cell is a male germ cell.

11. A method of producing mature male germ cells by administration of a compound to testicular tissue, wherein the compound is a compound of formula (I)

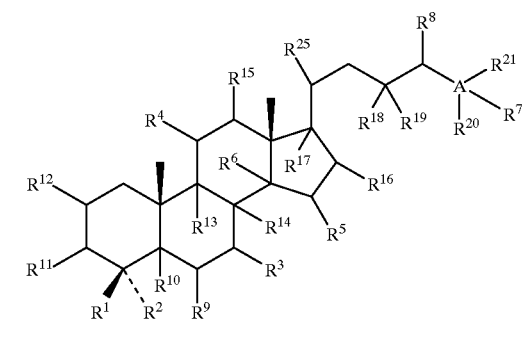

(I)

wherein $R^1$ and $R^2$, independently, are selected from the group consisting of hydrogen and branched or unbranched $C_1$–$C_6$ alkyl which may be substituted by halogen, hydroxy or cyano, or wherein $R^1$ and $R^2$ together designate methylene or, together with the carbon atom to which they are bound, form a cyclopropane ring, a cyclopentane ring, or a cyclohexane ring; $R^3$ is selected from the group consisting of hydrogen, methylene, hydroxy, methoxy, acetoxy, oxo, =$NOR^{26}$ wherein $R^{26}$ is hydrogen or $C_1$–$C_3$ alkyl, halogen, and $C_1$–$C_4$ alkyl; $R^4$ is selected from the group consisting of hydrogen, methylene, hydroxy, methoxy, acetoxy, oxo, =$NOR^{27}$ wherein $R^{27}$ is hydrogen or $C_1$–$C_3$ alkyl, halogen, and $C_1$–$C_4$ alkyl; $R^5$ designates, together with $R^6$, an additional bond between the carbon atoms to which $R^5$ and $R^6$ are bound; $R^9$ is hydrogen; $R^{10}$ is hydrogen; $R^{11}$ is selected from the group consisting of hydroxy, alkoxy, substituted alkoxy, alkanoyloxyalkyl, acyloxy, sulphonyloxy, phosphonyloxy, oxo, =$NOR^{28}$ wherein $R^{28}$ is hydrogen or $C_1$–$C_3$ alkyl, halogen and $C_1$–$C_4$ alkyl; $R^{12}$ is selected from the group consisting of hydrogen, $C_1$–$C_3$ alkyl, vinyl, $C_1$–$C_3$ alkoxy and halogen; $R^{13}$ designates, together with $R^{14}$, an additional bond between the carbon atoms to which $R^{13}$ and $R^{14}$ are bound; $R^{15}$ is selected from the group consisting of hydrogen, $C_1$–$C_4$ alkyl, methylene, hydroxy, methoxy, acetoxy, oxo, and =$NOR^{23}$ wherein $R^{23}$ is hydrogen or $C_1$–$C_3$ alkyl; $R^{16}$ is selected from the group consisting of hydrogen, $C_1$–$C_3$ alkyl, methylene, hydroxy, methoxy, oxo and =$NOR^{24}$ wherein $R^{24}$ is hydrogen or $C_1$–$C_3$ alkyl; $R^{17}$ is hydrogen or hydroxyl; $R^{18}$ and $R^{19}$ are, independently, hydrogen or fluoro; $R^{25}$ is selected from the group consisting of hydrogen, $C_1$–$C_4$ alkyl, methylene, hydroxy and oxo; A is a carbon atom, $R^7$ is selected from the group consisting of hydrogen, hydroxy and fluoro, and $R^8$ is selected from the group consisting of hydrogen, $C_1$–$C_4$ alkyl, methylene and halogen; $R^{20}$ is selected from the group consisting of $C_1$–$C_4$ alkyl, trifluoromethyl and $C_3$–$C_6$ cycloalkyl and $R^{21}$ is selected from the group consisitning of $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl; provided that the compound of formula (I) does not have any cumulated double bonds and further provided that the compound is not one of the following compounds:

Cholesta-8,14-diene-3β-ol; 4-Methylcholesta-8,14-diene-3β-ol; 4-Ethylcholesta-8,14-diene-3β-ol; 4,4-Dimethylcholesta-8,14-diene-3β-ol; 4β-Methyl-4β-ethylcholesta-8,14-diene-3β-ol; 4α-Ethyl-4β-methylcholesta-8,14-diene-3β-ol; 4,4-Diethylcholesta-8,14-diene-3β-ol; 4-Propylcholesta-8,14-diene-3β-ol; 4-Butylcholesta-8,14-diene-3β-ol; 4-Isobutylcholesta-8,14-diene-3β-ol; 4,4-Tetramethylenecholesta-8,14-diene-3β-ol; and 4,4-Pentamethylenecholesta-8,14-diene-3β-ol;

or esters or ethers thereof.

12. A method of promoting meiotic maturation in an oocyte, comprising culturing the oocyte in the presence of a compound of formula (I)

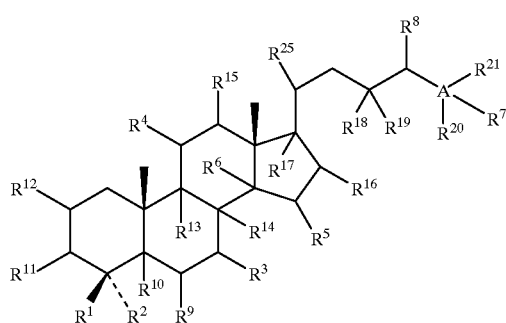

wherein $R^1$ and $R^2$, independently, are selected from the group consisting of hydrogen and branched or unbranched $C_1$–$C_6$ alkyl which may be substituted by halogen, hydroxy or cyano, or wherein $R^1$ and $R^2$ together designate methylene or, together with the carbon atom to which they are bound, form a cyclopropane ring, a cyclopentane ring, or a cyclohexane ring; $R^3$ is selected from the group consisting of hydrogen, methylene, hydroxy, methoxy, acetoxy, oxo, =$NOR^{26}$ wherein is hydrogen or $C_1$–$C_3$ alkyl, halogen, and $C_1$–$C_4$ alkyl; $R^4$ is selected from the group consisting of hydrogen, methylene, hydroxy, methoxy, acetoxy, oxo, =$NOR^{27}$ wherein $R^{27}$ is hydrogen or $C_1$–$C_3$ alkyl, halogen, and $C_1$–$C_4$ alkyl; $R^5$ designates, together with $R^6$, an additional bond between the carbon atoms to which $R^5$ and $R^6$ are bound; $R^9$ is hydrogen; $R^{10}$ is hydrogen; $R^{11}$ is selected from the group consisting of hydroxy, alkoxy, substituted alkoxy, alkanoyloxyalkyl, acyloxy, sulphonyloxy, phosphonyloxy, oxo, =$NOR^{28}$ wherein $R^{28}$ is hydrogen or $C_1$–$C_3$ alkyl, halogen and $C_1$–$C_4$ alkyl; $R^{12}$ is selected from the group consisting of hydrogen, $C_1$–$C_3$ alkyl, vinyl, $C_1$–$C_3$ alkoxy and halogen; $R^{13}$ designates, together with $R^{14}$, an additional bond between the carbon atoms to which $R^{13}$ and $R^{14}$ are bound; $R^{15}$ is selected from the group consisting of hydrogen, $C_1$–$C_4$ alkyl, methylene, hydroxy, methoxy, acetoxy, oxo, and =$NOR^{23}$ wherein $R^{23}$ is hydrogen or $C_1$–$C_3$ alkyl; $R^{16}$ is selected from the group consisting of hydrogen, $C_1$–$C_3$ alkyl, methylene, hydroxy, methoxy, oxo and =$NOR^{24}$ wherein $R^{24}$ is hydrogen or $C_1$–$C_3$ alkyl; $R^{17}$ is hydrogen or hydroxy; $R^{18}$ and $R^{19}$ are, independently, hydrogen or fluoro; $R^{25}$ is selected from the group consisting of hydrogen, $C_1$–$C_6$ alkyl, methylene, hydroxy and oxo; A is a carbon atom, $R^7$ is selected from the group consisting of hydrogen, hydroxy and fluoro, and $R^8$ is selected from the group consisting of hydrogen, $C_1$–$C_4$ alkyl, methylene and halogen; $R^{20}$ is selected from the group consisting of $C_1$–$C_4$ alkyl, trifluoromethyl and $C_3$–$C_6$ cycloalkyl and $R^{21}$ is selected from the group consisitning of $C_1$–$C_4$ alkyl, $C_1$–$C_4$ hydroxyalkyl, $C_1$–$C_4$ haloalkyl containing up to three halogen atoms, methoxymethyl, acetoxymethyl, and $C_3$–$C_6$ cycloalkyl; provided that the compound of formula (I) does not have any cumulated double bonds and further provided that the compound is not one of the following compounds:

Cholesta-8,14-diene-3β-ol; 4-Methylcholesta-8,14-diene-3β-ol; 4-Ethylcholesta-8,14-diene-3β-ol; 4,4-Dimethylcholesta-8,14-diene-3β-ol; 4α-Methyl-4β-ethylcholesta-8,14-diene-3β-ol; 4α-Ethyl-4β-methylcholesta-8,14-diene-3β-ol; 4,4-Diethylcholesta-8,14-diene-3β-ol; 4-Propylcholesta-8,14-diene-3β-ol; 4-Butylcholesta-8,14-diene-3β-ol; 4-Isobutylcholesta-8,14-diene-3β-ol; 4,4-Tetramethylenecholesta-8,14-diene-3β-ol; and 4,4-Pentamethylenecholesta-8,14-diene-3β-ol;

or esters or ethers thereof.

* * * * *